(12) United States Patent
Kimura et al.

(10) Patent No.: US 11,604,332 B2
(45) Date of Patent: Mar. 14, 2023

(54) IMAGING DEVICE AND ELECTRONIC APPARATUS

(71) Applicant: SONY SEMICONDUCTOR SOLUTIONS CORPORATION, Kanagawa (JP)

(72) Inventors: Katsuji Kimura, Kanagawa (JP); Yuki Urano, Kanagawa (JP)

(73) Assignee: SONY SEMICONDUCTOR SOLUTIONS CORPORATION, Kanagawa (JP)

( * ) Notice: Subject to any disclaimer, the term of this patent is extended or adjusted under 35 U.S.C. 154(b) by 206 days.

(21) Appl. No.: 17/044,973

(22) PCT Filed: Mar. 28, 2019

(86) PCT No.: PCT/JP2019/013538
§ 371 (c)(1),
(2) Date: Oct. 2, 2020

(87) PCT Pub. No.: WO2019/198524
PCT Pub. Date: Oct. 17, 2019

(65) Prior Publication Data
US 2021/0165237 A1 Jun. 3, 2021

(30) Foreign Application Priority Data
Apr. 11, 2018 (JP) .............................. JP2018-075930

(51) Int. Cl.
*G02B 13/00* (2006.01)
*G02B 23/24* (2006.01)
(Continued)

(52) U.S. Cl.
CPC ....... *G02B 13/0015* (2013.01); *G02B 23/243* (2013.01); *G02B 27/646* (2013.01);
(Continued)

(58) Field of Classification Search
CPC .............. G02B 13/0015; G02B 23/243; G02B 23/2484; G02B 27/644; G02B 27/646;
(Continued)

(56) References Cited

U.S. PATENT DOCUMENTS

2005/0122401 A1   6/2005   Horie
2008/0074770 A1   3/2008   Uchiyama
(Continued)

FOREIGN PATENT DOCUMENTS

CN   101604072 A   12/2009
CN   102187261 A    9/2011
(Continued)

OTHER PUBLICATIONS

International Search Report and Written Opinion prepared by the Japanese Patent Office dated Jun. 4, 2019, for International Application No. PCT/JP2019/013538.

*Primary Examiner* — Amy R Hsu
(74) *Attorney, Agent, or Firm* — Sheridan Ross P.C.

(57) ABSTRACT

The present technology relates to an imaging device and an electronic apparatus capable of adjusting a focus position and an image stabilization position with high accuracy. There are provided a lens that converges object light, an imaging element that photoelectrically converts the object light received from the lens, a circuit base that includes a circuit configured to output a signal received from the imaging element to an outside, an actuator that drives the lens with a PWM (Pulse Width Modulation) waveform in at least either one of an X-axis direction and a Y-axis direction, and plural detection units that are so disposed as to face plural first coils included in the actuator, and detect magnetic fields generated by the first coils. The present technology is applicable to an imaging device.

12 Claims, 24 Drawing Sheets

(51) Int. Cl.
*H04N 5/225* (2006.01)
*G03B 3/10* (2021.01)
*G02B 27/64* (2006.01)
*G03B 5/00* (2021.01)

(52) U.S. Cl.
CPC ............ *G03B 3/10* (2013.01); *G03B 5/00* (2013.01); *H04N 5/2254* (2013.01); *G03B 2205/0015* (2013.01); *G03B 2205/0023* (2013.01); *G03B 2205/0069* (2013.01); *H04N 2005/2255* (2013.01)

(58) Field of Classification Search
CPC .. G02B 7/023; G02B 7/08; G03B 2205/0015; G03B 2205/0023; G03B 2205/0069; G03B 3/10; G03B 30/00; G03B 5/00; H04N 13/239; H04N 2005/2255; H04N 5/2253; H04N 5/2257; H04N 5/232
See application file for complete search history.

(56) References Cited

U.S. PATENT DOCUMENTS

| | | | | |
|---|---|---|---|---|
| 2010/0091120 | A1* | 4/2010 | Nagata | H04N 5/2257 359/557 |
| 2010/0253825 | A1 | 10/2010 | Horie | |
| 2012/0019680 | A1* | 1/2012 | Shimada | H04N 5/232 348/208.99 |
| 2014/0186017 | A1 | 7/2014 | Shibata | |
| 2015/0171128 | A1 | 6/2015 | Ogata | |
| 2017/0133423 | A1 | 5/2017 | Ogata | |
| 2017/0154910 | A1 | 6/2017 | Ogata | |
| 2018/0149881 | A1* | 5/2018 | Kim | H02K 41/0356 |
| 2018/0157004 | A1* | 6/2018 | Huang | G02B 7/09 |
| 2018/0321459 | A1* | 11/2018 | Kim | G03B 3/10 |
| 2019/0339542 | A1* | 11/2019 | Murakami | G02B 7/08 |
| 2020/0195815 | A1* | 6/2020 | Lee | H01F 7/06 |
| 2020/0304715 | A1* | 9/2020 | Fushida | H04N 5/23258 |
| 2020/0374428 | A1* | 11/2020 | Saito | G02B 7/28 |
| 2021/0165237 | A1* | 6/2021 | Kimura | A61B 1/00188 |
| 2022/0043235 | A1* | 2/2022 | Park | G03B 3/10 |

FOREIGN PATENT DOCUMENTS

| | | |
|---|---|---|
| JP | 2005-121838 | 5/2005 |
| JP | 2007-151862 | 6/2007 |
| JP | 2014-126860 | 7/2014 |
| JP | 2015-115522 | 6/2015 |
| JP | 2015-197627 | 11/2015 |
| KR | 10-2017-0062196 | 6/2017 |

\* cited by examiner

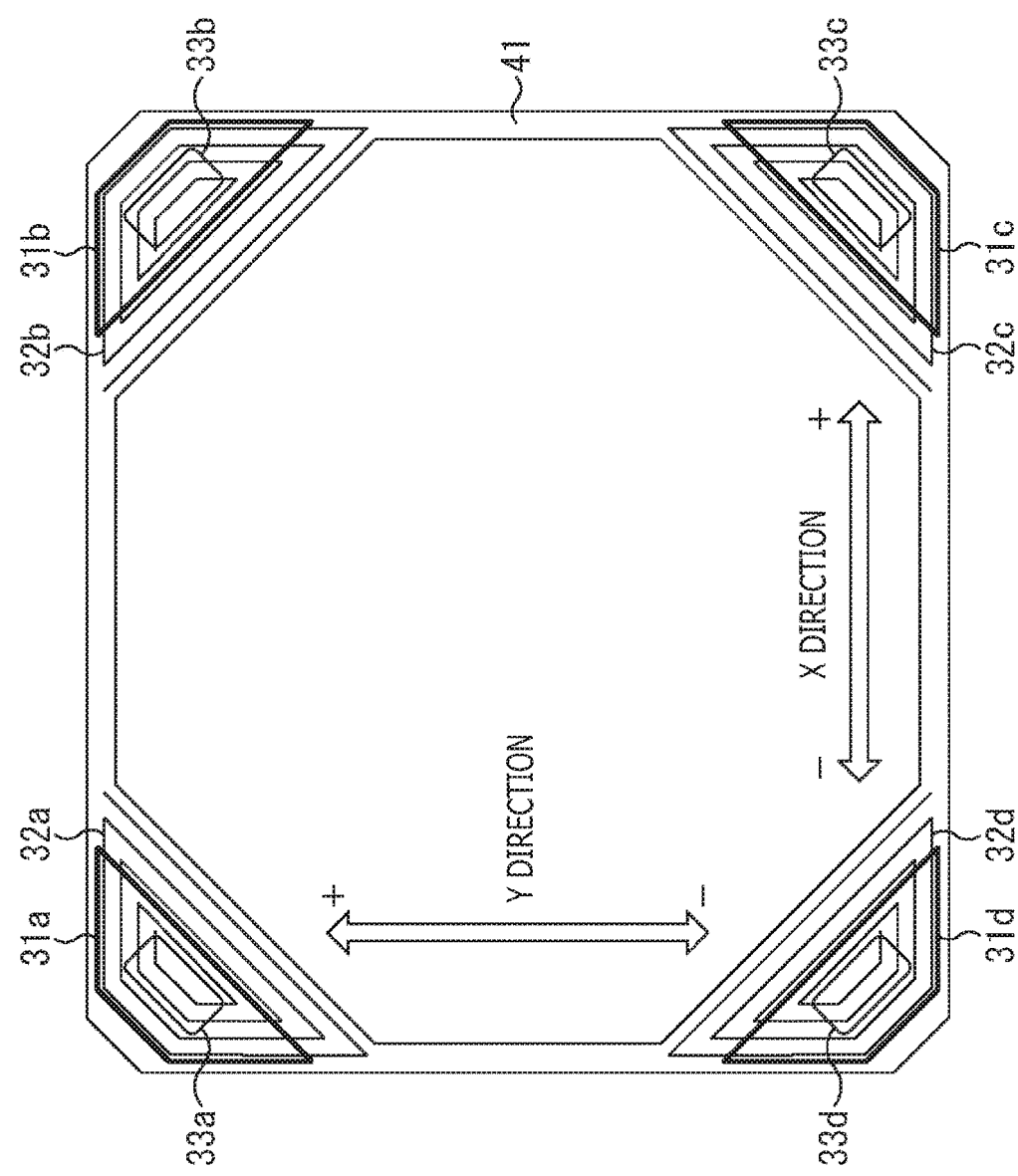
F I G. 4

IMAGING DEVICE AND ELECTRONIC APPARATUS

CROSS REFERENCE TO RELATED APPLICATIONS

This application is a national stage application under 35 U.S.C. 371 and claims the benefit of PCT Application No. PCT/JP2019/013538 having an international filing date of 28 Mar. 2019, which designated the United States, which PCT application claimed the benefit of Japanese Patent Application No. 2018-075930 filed 11 Apr. 2018, the entire disclosures of each of which are incorporated herein by reference.

TECHNICAL FIELD

The present technology relates to an imaging device and an electronic apparatus, such as an imaging device and an electronic apparatus capable of controlling a position of a lens with high accuracy.

BACKGROUND ART

Recently, high-pixelization, performance improvement, miniaturization, and the like of an imaging device are in progress. With high-pixelization and performance improvement of the imaging device, power consumption of an imaging element mounted on the imaging device, such as a CCD (Charge-Coupled Device) sensor and a CMOS (Complementary Metal-Oxide-Semiconductor) image sensor, is increasing.

Power consumption of an actuator or the like for driving a lens focus is also increasing. Accordingly, power consumption by the imaging device also tends to increase.

A method currently proposed for reducing power consumption generates a driving signal having a PWM (Pulse Width Modulation) waveform for the actuator to reduce power consumption to approximately a half. However, a magnetic field is produced when the actuator is driven by PWM driving. It is known that this magnetic field becomes a disturbing factor for the imaging element, and causes noise contamination.

For reducing noise, it has been proposed to synchronize a driving waveform of the imaging element with an auto focus driver generating a PWM signal, and output a PWM waveform in a dead zone range during a driving time of the imaging element to reduce noise.

It is also proposed as one method for improving performance of the imaging device to mount an element for position detection, such as a Hall element, on the actuator and output a position of a lens to the outside to constantly detect a focus position of the lens and rapidly shifting the lens to a position for converging object light.

For example, PTL 1 proposes implementation of auto focus based on a focus change of a lens by driving the lens while controlling a driving element (actuator) by a PWM signal generated from a focus driving circuit. PTL 1 also proposes equipment of a Hall element for high-performance position detection of a lens.

PTL 2 proposes noise reduction by using a metal plate for cutting off (shielding) a magnetic field generated by PWM driving of an actuator to reduce noise of an imaging element produced by the magnetic field.

PTL 3 proposes detection of a lens position using a PWM signal (alternating current signal) according to electromotive force of a detection coil so disposed as to face excitation power. According to this proposal, the detection coil is provided on the operating lens side, and a position is detected on the basis of a phase of electromotive current generated by parallel shifts of an excitation coil and the detection coil.

CITATION LIST

Patent Literature

[PTL 1]
    JP 2011-022563A
[PTL 2]
    JP 2014-082682A
[PTL 3]
    JP 2000-295832A

SUMMARY

Technical Problems

According to PTL 1, equipment of the Hall element is required. In this case, miniaturization is difficult to achieve with a size increase of the actuator. Moreover, the necessity of providing the Hall element may raise costs of the imaging device.

According to PTL 2, the metal plate for cutting off the magnetic field is made of gold, silver, copper, aluminum or the like, and therefore may raise costs of the imaging device. Moreover, the metal plate provided for cutting off the magnetic field does not contribute to miniaturization of the imaging device.

An actuator available in recent years is structured such that a coil is disposed outside a lens, and shifts perpendicularly to an imaging element according to excitation power to achieve focus detection. When PTL 3 is applied to such a structure, the lens position is difficult to detect by the parallel shifts of the excitation power coil and the detection coil so disposed as to face each other. Accordingly, PTL 3 is difficult to apply to the actuator available in recent years.

The present technology has been developed in consideration of the aforementioned circumstances, and is aimed at providing an imaging device capable of achieving performance improvement, low power consumption, and miniaturization.

Solution to Problems

An imaging device according to one aspect of the present technology includes a lens that converges object light, an imaging element that photoelectrically converts the object light received from the lens, a circuit base that includes a circuit configured to output a signal received from the imaging element to an outside, an actuator that drives the lens with a PWM (Pulse Width Modulation) waveform in at least either one of an X-axis direction and a Y-axis direction, and plural detection units that are so disposed as to face plural first coils included in the actuator, and detect magnetic fields generated by the first coils.

An electronic apparatus according to one aspect of the present technology includes an imaging device. The imaging device includes a lens that converges object light, an imaging element that photoelectrically converts the object light received from the lens, a circuit base that includes a circuit configured to output a signal received from the imaging element to an outside, an actuator that drives the lens with a PWM (Pulse Width Modulation) waveform in at least either one of an X-axis direction and a Y-axis direction, and plural detection units that are so disposed as to face plural first coils included in the actuator, and detect magnetic fields generated by the first coils.

The imaging device of the one aspect of the present technology includes the lens that converges object light, the imaging element that photoelectrically converts the object light received from the lens, the circuit base that includes a circuit configured to output a signal received from the imaging element to the outside, the actuator that drives the lens with a PWM (Pulse Width Modulation) waveform in at least either one of the X-axis direction and the Y-axis direction, and the plural detection units that are so disposed as to face the plural coils included in the actuator, and detect magnetic fields generated by the coils.

The electronic apparatus according to the one aspect of the present technology includes the imaging device.

Note that each of the imaging device and the electronic apparatus may be an independent apparatus, or an internal block constituting one apparatus.

Advantageous Effects of Invention

According to one aspect of the present technology, an imaging device capable of achieving performance improvement, low power consumption, and miniaturization can be provided.

Note that advantageous effects to be produced are not limited to the advantageous effects described herein, but may be any advantageous effects described in the present disclosure.

BRIEF DESCRIPTION OF DRAWINGS

FIG. 4 is a diagram explaining a board on which the position detection coils are provided.

DESCRIPTION OF EMBODIMENTS

Modes for carrying out the present technology (hereinafter, referred to as embodiments) will be described below.
<Configuration of Imaging Device>

The present technology is applicable to an imaging device including an imaging element such as a CCD (Charge-Coupled Device) sensor and a CMOS (Complementary Metal-Oxide-Semiconductor) image sensor. In addition, the present technology is applicable to an apparatus including such an imaging device, for example, a portable terminal apparatus and the like.

Figure 1:
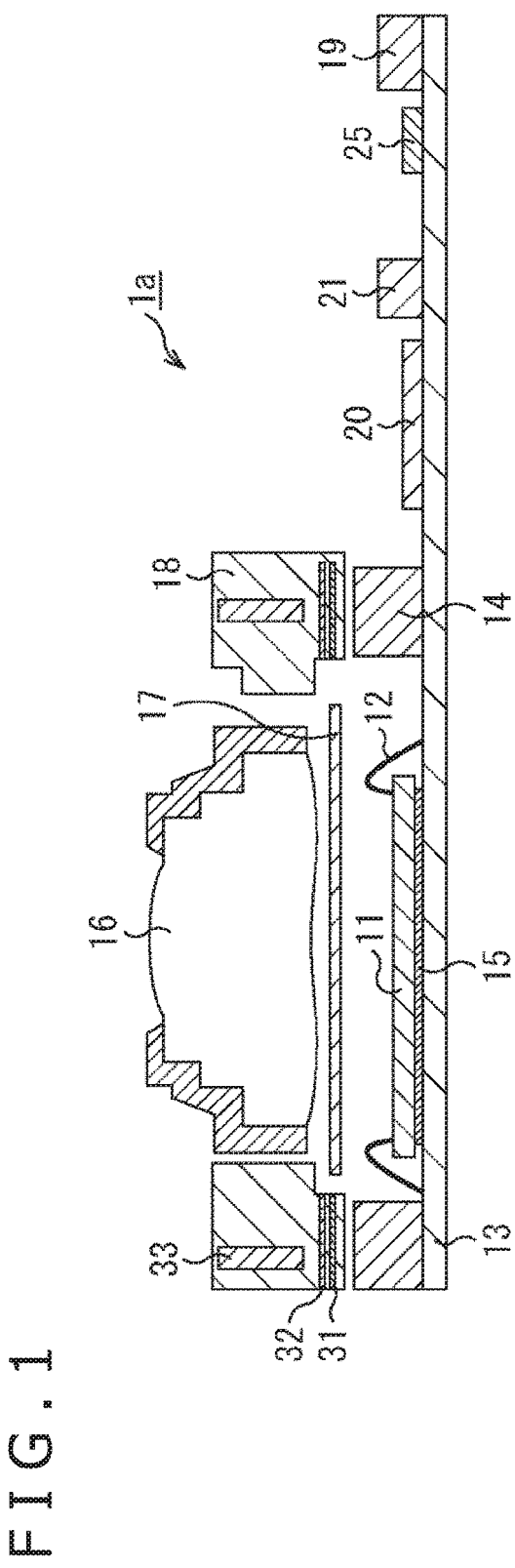
FIG. 1 is a diagram depicting a configuration of an imaging device according to one embodiment to which the present technology is applied.

FIG. 1 is a diagram depicting a configuration of an imaging device of one embodiment according to one aspect of the present technology. An imaging device 1a depicted in FIG. 1 includes an imaging element 11, such as a CCD sensor and a CMOS image sensor, which photoelectrically converts object light received from an object to image the object.

In addition, the imaging device 1a includes a lens 16 which converges object light, and an infrared cut filter 17 for cutting off infrared light from a light signal having passed through the lens 16. Further, the imaging device 1a includes an actuator 18 which drives the lens upward and downward (hereinafter, referred to as a Z-axis direction where appropriate) in a direction of the imaging element 11 to adjust a focus of the lens 16.

Moreover, the actuator 18 has a correction function of reducing an effect of hand-vibration by driving in a direction (hereinafter, referred to as an X-axis direction or a Y-axis direction) of a horizontal plane (hereinafter, referred to as an X-Y plane where appropriate) with respect to an imaging surface of the imaging element 11.

Additionally, the imaging device 1a includes a gyro sensor 21 which senses hand-vibration, an auto-focus OIS driver 20 for controlling the actuator 18 from the outside, and a circuit board 13 for outputting an electric signal of the imaging element 11 to the outside. Note that the circuit board 13 expressed as a circuit board here is not limited to a plate-shaped board, but may be a circuit base.

OIS is an abbreviation of Optical Image Stabilizer, and refers to optical image stabilization as a method performed by an optical system to achieve correction for reducing an effect of hand-vibration on the imaging device 1a. The optical image stabilization senses vibration during imaging using the gyro sensor 21, and reduces the effect of hand-vibration by adjusting the position of the lens 16 and the position of the imaging element 11. The description continues here while presenting an example of image stabilization achieved by adjusting the position of the lens 16.

The imaging device 1a further includes a metal wire 12 for electrically connecting the imaging element 11 and the circuit board 13, an adhesive 15 for fixing the imaging element 11 and the circuit board 13, and a spacer 14 for fixing the actuator 18 described above and the circuit board 13.

The auto-focus OIS driver 20 described above has a function of outputting a PWM (Pulse Width Modulation) waveform to the actuator 18 to reduce power consumed by the imaging device 1a. The actuator 18 has a function of driving the focus of the lens 16 according to the input PWM waveform.

The circuit board 13 has a function of detecting induced electromotive force produced by a magnetic field generated by the PWM waveform, and has a function of detecting the position of the lens 16 on the basis of the detected induced electromotive force. The circuit board 13 further has a function of achieving a high-performance focus shift of the lens by outputting a detected result to the outside.

The storage unit 25 stores data for correcting variations of the imaging device 1a. For example, an amount of induced electromotive force used for lens position adjustment varies on the basis of the number and size of windings of a coil 24 (FIG. 2) of the actuator 18, a forming state of position detection coils 32 (FIG. 2), and the like. Accordingly, variations of the induced electromotive force may be measured during manufacture of the imaging device 1a, and adjustment values for adjusting the variations may be stored in a storage unit 25. Thereafter, the adjustment values stored in the storage unit 25 may be used to perform a process for correcting variations of the individual imaging devices 1a during real control.

The imaging device 1a includes fine pattern coils 31 (hereinafter, referred to as FP coils 31) disposed to drive the lens 16 in a plane identical to the plane of the imaging element 11 (X-Y plane) for image stabilization. Force is generated in a direction horizontal to the imaging element 11 between the FP coils 31 and magnets 33 by supplying current to the FP coils 31. As a result, the lens 16 shifts in the plane identical to the plane of the imaging element 11.

Further, the imaging device 1a to which the present technology is applied includes the position detection coils 32 for detecting the position of the lens 16 in the X-Y plane. The position detection coils 32 are provided between the FP coils 31 and the magnets 33.

Figure 2:
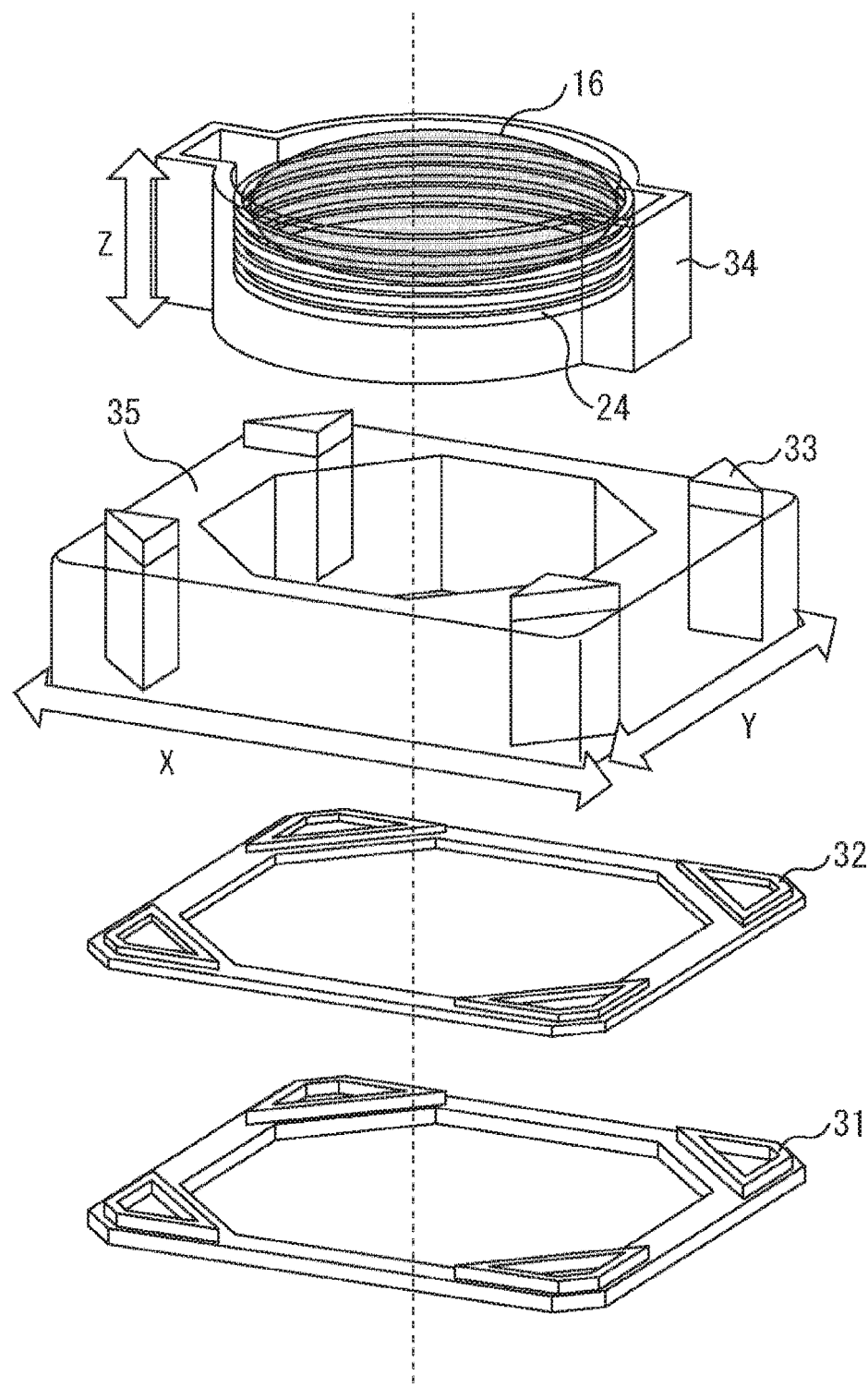
FIG. 2 is a diagram depicting a configuration example of an actuator.

Described with reference to FIG. 2 will be a configuration of a portion associated with driving of the lens 16 in an auto-focus direction (Z-axis direction) and an image stabilization direction (X-Y plane), and a portion associated with position detection of the lens 16.

The actuator 18 (FIG. 1) has a voice coil motor structure, while the coil 24 has a structure supported by a spring (not illustrated). The coil 24 is provided on a side surface of a lens holder 34. The lens holder 34 holds the lens 16 inside.

The coil 24 is provided on the side surface of the lens holder 34, while the magnets 33 are provided on a side opposite to the coil 24. The magnets 33 are provided inside an OIS holder 35. The lens holder 34 is housed inside the OIS holder 35.

When current flows in the coil 24, force is generated in an up-down direction (Z direction) in the figure. The lens 16 held by the lens holder 34 is shifted upward or downward by the generated force. As a result, a distance between the lens 16 and the imaging element 11 changes. Auto focus (AF: Auto-Focus) is achieved by such a mechanism.

The position detection coils 32 are provided on a bottom surface of the OIS holder 35. Each of the position detection coils 32 is a part constituting a corner of the OIS holder 35, and is provided below the corresponding magnet 33. The position detection coils 32 may be directly provided on the bottom surface of the OIS holder 35 (may be formed integrally with the OIS holder 35), or may be constituted by one-piece member (one layer) and laminated on the bottom surface of the OIS holder 35 as depicted in FIG. 2.

The FP coils 31 are provided below the position detection coils 32. The magnets 33 are provided on a side facing the FP coils 31. When current flows in the FP coils 31, force is generated in a left-right direction (X-Y plane direction) in the figure. The generated force shifts the lens 16 (OIS holder 35) held by the lens holder 34 is shifted in up-down and left-right directions in the X-Y plane to be shifted in a direction for reducing an effect of disturbance such as hand-vibration. Image stabilization is achieved by such a mechanism.

<Detection of Induced Electromotive Force>

Figure 3:
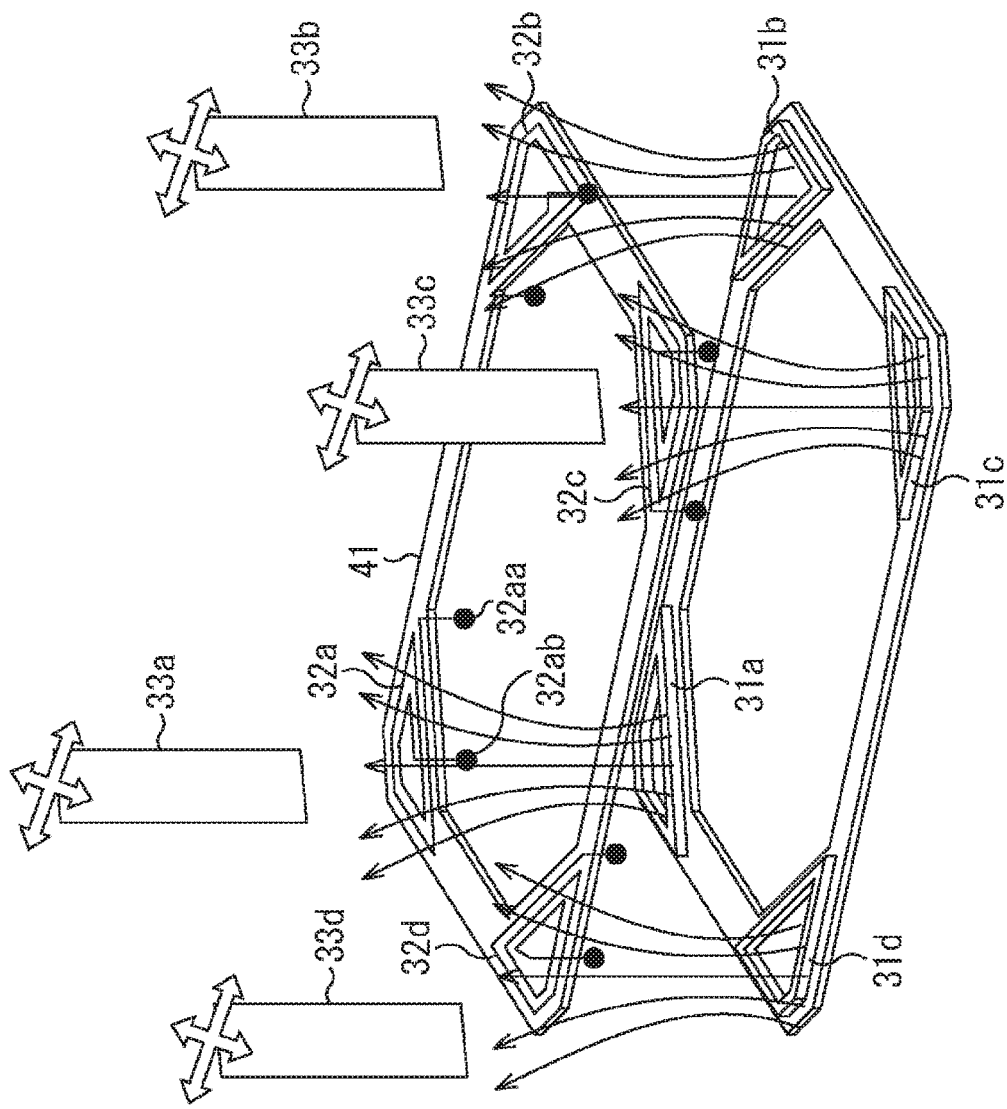
FIG. 3 is a diagram explaining magnetic fields received by position detection coils.

FIG. 3 is a diagram for explaining magnetic fields generated by a PWM waveform, and induced electromotive force generated by these magnetic fields. FIG. 3 depicts magnetic fields generated in the FP coils 31, and explains induced electromotive force generated in the position detection coils 32.

More reduction of power consumption of current flowing in the coil 24 and the FP coils 31 is achievable in a case of a signal of PWM waveform driving (signal switching between Hi and Low in a predetermined cycle) than in a case of a signal having a fixed voltage value (signal maintaining Hi state at all times) as a signal continuing Hi state.

Therefore, in a case where a signal of PWM waveform driving is adopted as a signal supplied to the coil 24 and the FP coils 31 to reduce power consumption, magnetic fields are generated in respective directions as depicted in FIG. 3. Referring to FIG. 3, magnetic fields generated in the FP coils 31 are magnetic fields directed from the imaging element 11 (not depicted in FIG. 3) located below the FP coils 31 toward the lens 16 (not depicted in FIG. 3) located above the position detection coils 32 in FIG. 3.

Note that magnetic fields are generated in directions different from the directions depicted in FIG. 3 depending on directions of the current. The description continues here while presenting the example that the magnetic fields are generated in the directions depicted in FIG. 3 by way of example.

The magnetic fields generated in the coil 24 and the FP coils 31 pass through the imaging element 11 (FIG. 1). Accordingly, the magnetic fields affect an image captured by the imaging element 11 in some cases. For example, noise may be produced by an effect of the magnetic fields, and an image (image signal) contaminated with noise may be output from the imaging element 11.

An effect of noise produced by the magnetic fields can be reduced by synchronizing PWM waveform driving with a driving signal of the imaging element 11 and preventing generation of magnetic fields during a period of driving producing noise of the imaging element 11. Such a synchronization achieves output of an image not affected by magnetic fields from the imaging device 1a.

The magnetic fields generated by supply of the signal of PWM waveform driving to the FP coils 31 also reach the position detection coils 32. Described will be a function of detecting the position of the lens 16 in the X-Y plane by detecting intensity of the magnetic fields reaching the position detection coils 32.

As depicted in FIG. 3, the position detection coils 32 are provided between the FP coils 31 and the magnets 33. Induced electromotive force is generated in the position detection coils 32 by providing the position detection coils 32 in a direction perpendicular to the magnetic fields generated by PWM waveform driving. The positions of the lens 16 (lens holder 34) in the X axis direction and the Y axis direction are detectable on the basis of intensity of the induced electromotive force.

Further, high-performance lens driving, i.e., image stabilization is achievable by detecting the position of the lens 16 (lens holder 34).

As depicted in FIG. 3, FP coils 31a to 31d are provided on a plane (X-Y plane) horizontal to the imaging surface of the imaging element 11. Moreover, magnets 33a to 33d are provided at such positions as to face the FP coils 31a to 31d, respectively. Furthermore, position detection coils 32a to 32d are provided between the FP coils 31a to 31d and the magnets 33a to 33d, respectively.

The FP coils 31a to 31d will be hereinafter simply referred to as FP coils 31 in a case of no necessity of distinction between the FP coils 31a to 31d. Similarly, the position detection coils 32a to 32d will be hereinafter simply referred to as position detection coils 32 in a case of no necessity of distinction between the position detection coils 32a to 32d. Similarly, the magnets 33a to 33d will be hereinafter simply referred to as magnets 33 in a case of no necessity of distinction between the magnets 33a to 33d.

The position detection coil 32a generates dielectric electromotive force by a magnetic field generated by current flowing in the FP coil 31a. The position detection coil 32b generates dielectric electromotive force by a magnetic field generated by current flowing in the FP coil 31b. The position detection coil 32c generates dielectric electromotive force by a magnetic field generated by current flowing in the FP coil 31c. The position detection coil 32d generates dielectric electromotive force by a magnetic field generated by current flowing in the FP coil 31d.

As described above, magnetic fields are generated in the FP coils 31a to 31d by current flowing in the FP coils 31a to 31d. As a result, induced electromotive force is generated in each of the position detection coils 32a to 32d. The positions of the lens 16 (lens holder 34) in the X-axis direction and the Y-axis direction (shift directions) are detectable on the basis of intensity of induced electromotive force generated in each of the position detection coils 32a to 32d.

FIG. 4 is a perspective view as a plan view in the X-Y plane as viewed from the position detection coil 32 side. As depicted in FIG. 4, the description continues here on an assumption that the position detection coils 32a to 32d are formed at corner portions of a board 41 having a quadrangular shape. However, each of the position detection coils 32a to 32d may be directly provided on a bottom surface of the OIS holder 35.

Each of the position detection coils 32a to 33d is provided on corresponding one of respective corners of the board 41 different from each other. The position detection coil 32a is provided at the upper left corner of the board 41 in FIG. 3. The position detection coil 32b is provided at the upper right corner (the corner facing the corner where the position detection coil 32a is provided in the X-axis direction) of the board 41 in FIG. 3.

The position detection coil 32c is provided at the lower right corner (the corner facing the corner where the position detection coil 32a is provided in an oblique direction) of the board 41 in FIG. 3. The position detection coil 32d is provided at the lower left corner (the corner facing the corner where the position detection coil 32a is provided in the Y-axis direction, and facing the corner where the position detection coil 32c is provided in the X-axis direction) of the board 41 in FIG. 3.

As described above, dielectric electromotive force is generated in the position detection coils 32 by providing the position detection coils 32 in the direction horizontal to the magnetic fields generated by PWM waveform driving. The positions of the lens 16 (lens holder) in the X-axis direction and the Y-axis direction (position in the X-Y plane) are detectable on the basis of intensity of the dielectric electromotive force.

Centers of the FP coils 31 and centers of the magnets 33 are substantially in alignment with each other when the lens 16 is located at a normal position in a stationary state. The centers of the FP coils 31 and centers of the position detection coils 32 deviate from each other when the lens 16 is located at the normal position in the stationary state. In FIG. 4, the centers of the FP coils 31 are located behind (outside) the centers of the position detection coils 32.

In other words, the centers of the FP coils 31 and the centers of the position detection coils 32 are located at positions aligned with each other when the lens 16 deviates from the normal position by an effect of hand-vibration or the like. When the centers of the FP coils 31 and the centers of the position detection coils 32 align with each other, the magnetic fields generated in the FP coils 31 are efficiently receivable by the position detection coils 32. In addition, the position detection coils 32 are provided to detect deviation of the lens 16 when the lens 16 deviates from the normal position. Accordingly, the position detection coils 32 are preferably provided at such positions that the magnetic fields generated in the FP coils 31 are most efficiently receivable when the lens 16 deviates from the normal position.

As apparent from the foregoing points, the centers of the FP coils 31 and the centers of the position detection coils 32 deviate from each other when the lens 16 is located at the normal position in the stationary state as described above. Note that the manner of deviation is presented here only by way of example, and may be another manner. Another example of this deviation will be described below with reference to FIG. 15.

In addition, the position detection coils 32 are larger in size than the FP coils 31. A positional relation between the FP coils 31 and the position detection coils 32 is not fixed but is variable by an effect such as disturbance. Accordingly, the position detection coils 32 are larger than the FP coils 31 so as to receive the magnetic fields generated in the FP coils 31 even with deviation of the positional relation.

Refer to FIG. 3 again. Each of the position detection coils 32 has a start point 32a and an end point 32b. The start point 32a and the end point 32b are connected to a detection circuit 50 (FIG. 6) not depicted in FIG. 3. The position detection coil 32a has a start point 32aa and an end point 32ab.

While reference signs are not given in FIG. 3, the position detection coil 32b has a start point 32ba and an end point 32bb. Similarly, the position detection coil 32c has a start point 32ca and an end point 32cb, and the position detection coil 32d has a start point 32da and an end point 32db.

Each of the position detection coils 32 has a loop shape. In this case, one of the start point 32a (e.g., start point 32aa) and the end point 32b (e.g., end point 32ab) is located inside the loop, while the other point 32a or 32b is located outside the loop to avoid overlap of lines.

Accordingly, for connecting the start point 32a and the end point 32b to the detection circuit 50, i.e., extracting a line from each of the start point 32a and the end point 32b, each of the position detection coils 32 needs to be formed across a plurality of layers.

On an assumption that the board 41 is constituted by one layer, the start point 32aa of the position detection coil 32a is located at a point outside the position detection coil 32a, while the end point is located in a center portion of the position detection coil 32a, for example. A line is difficult to extract from the end point located in the center portion of the position detection coil 32 without overlap with the formed position detection coil 32a.

Figure 5:
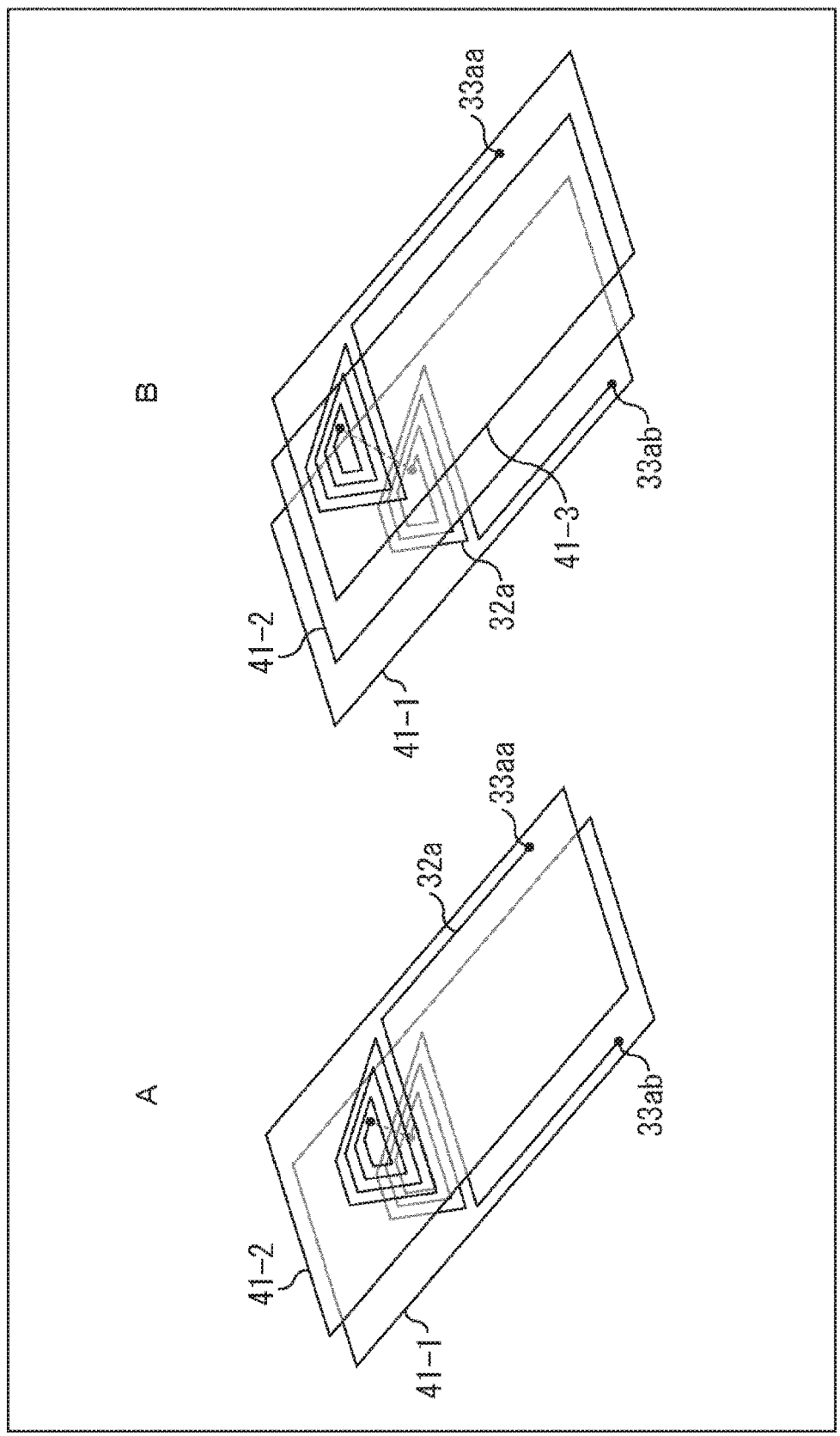
FIG. 5 illustrates diagrams explaining a configuration of the position detection coils provided on the board.

Accordingly, the board 41 is constituted by two layers as depicted in part A of FIG. 5. The description continues while presenting the position detection coil 32a by way of example in FIG. 5. Each of the other position detection coils 32b to 32d can be configured in a similar manner.

Suppose that the board 41 has two layers constituted by a board 41-1 and a board 41-2. The start point 32aa of the position detection coil 32a is provided on the board 41-1. A coil is formed in a loop shape extending from the start point 32aa in a direction from the outside to the inside.

Further, an end point of the position detection coil 32 in the first layer is formed at a center portion of the position detection coil 32a provided on the board 41-1. A start point of the position detection coil 32 in the second layer is connected to this end position. The position detection coil 32a is provided in a loop shape extending from the start point in a direction from the inside to the outside on the board 41-2 in the second layer.

The position detection coil 32a in the loop shape is provided from the start point 32aa formed on the board 41-1 to the end point 32ab formed on the circuit board 13-2. Further, connection to the not-depicted detection circuit 50 is allowed by using the start point 32aa formed on the board 41 and the end point 32ab formed on the board 41-2.

The start point and the end point of each of the position detection coils 32b to 32d are formed similar to the start point 32aa and the end point 32ab of the position detection coil 32a. In addition, this configuration of the position detection coils 32 is also applicable to the FP coils 31.

While the example depicted in part A of FIG. 5 is an example of the board 41 constituted by two layers, the board 41 may be constituted by three layers as depicted in part B of FIG. 5. According to the example depicted in part B of FIG. 5, the board 41 has three layers constituted by the boards 41-1 to 41-3. The position detection coil 32a having a loop shape is formed on each of the boards 41. The position detection coil 32a in each of the layers forms the one connected position detection coil 32a.

Moreover, as depicted in part B of FIG. 5, in a case where the board 41 is constituted by three layers, the position detection coil 32a may be provided on each of the board 41-1 in the first layer and the board 41-3 in the third layer, while the board 41-2 in the second layer may be used as a circuit dedicated for outputting an electric signal from the imaging element 11 to the outside without equipped with the position detection coil 32a, for example.

In the case of such a configuration, a wire for connecting the position detection coil 32a provided on the circuit board 41-1 and the position detection coil 32a provided on the board 41-3 is formed on the circuit board 41-2.

While the board 41 constituted by two layers or three layers has been presented here by way of example, the board 41 may be constituted by multiple layers such as four or five layers.

As described above, the board 41 is allowed to have a plurality of layers, and each of the position detection coils 32 is providable across the plurality of layers. Moreover, the number of layers and the layer configuration of the board 41 may be either the number of layers and the layer configuration presented here by way of example, or may be other numbers and other layer configurations.

When current flows in the FP coils 31 (FIG. 3) constituting a part of the actuator 18, magnetic fields are generated and flow into the position detection coils 32 configured as above. As a result, induced electromotive force is generated in the position detection coils 32. The induced electromotive force thus generated can be calculated utilizing Faraday's law.

When a magnetic flux penetrating a coil having the number of windings of N varies by $\Delta\phi[Wb]$ in $\Delta t[s]$, induced electromotive force V[V] generated in the coil is expressed by following Equation (1).

$$V = -N \cdot \Delta\phi / \Delta t \tag{1}$$

As apparent from Equation (1), induced electromotive force increases as the number of windings N becomes larger. The number of windings increases by providing the position detection coils 32 across a plurality of layers of the board 41 as described above. With the increase in the number of windings, induced electromotive force is allowed to increase. In this configuration, therefore, generated induced electromotive force is easily detectable.

A configuration of the detection circuit 50 connected to the position detection coils 32 configured as above will be described. Note that following description continues while presenting the board 41 constituted by one layer as viewed in the figure. However, the board 41 is constituted by a plurality of layers as described above.

While FIG. 4 presents the case where the four position detection coils 32a to 33d are provided by way of example, the two position detection coils 32 may be provided. The case where the two position detection coils 32 are provided will be described below with reference to FIG. 9. The description continues while initially presenting the case where the four position detection coils 32a to 33d are provided here.

<Configuration of Detection Circuit>

Figure 6:
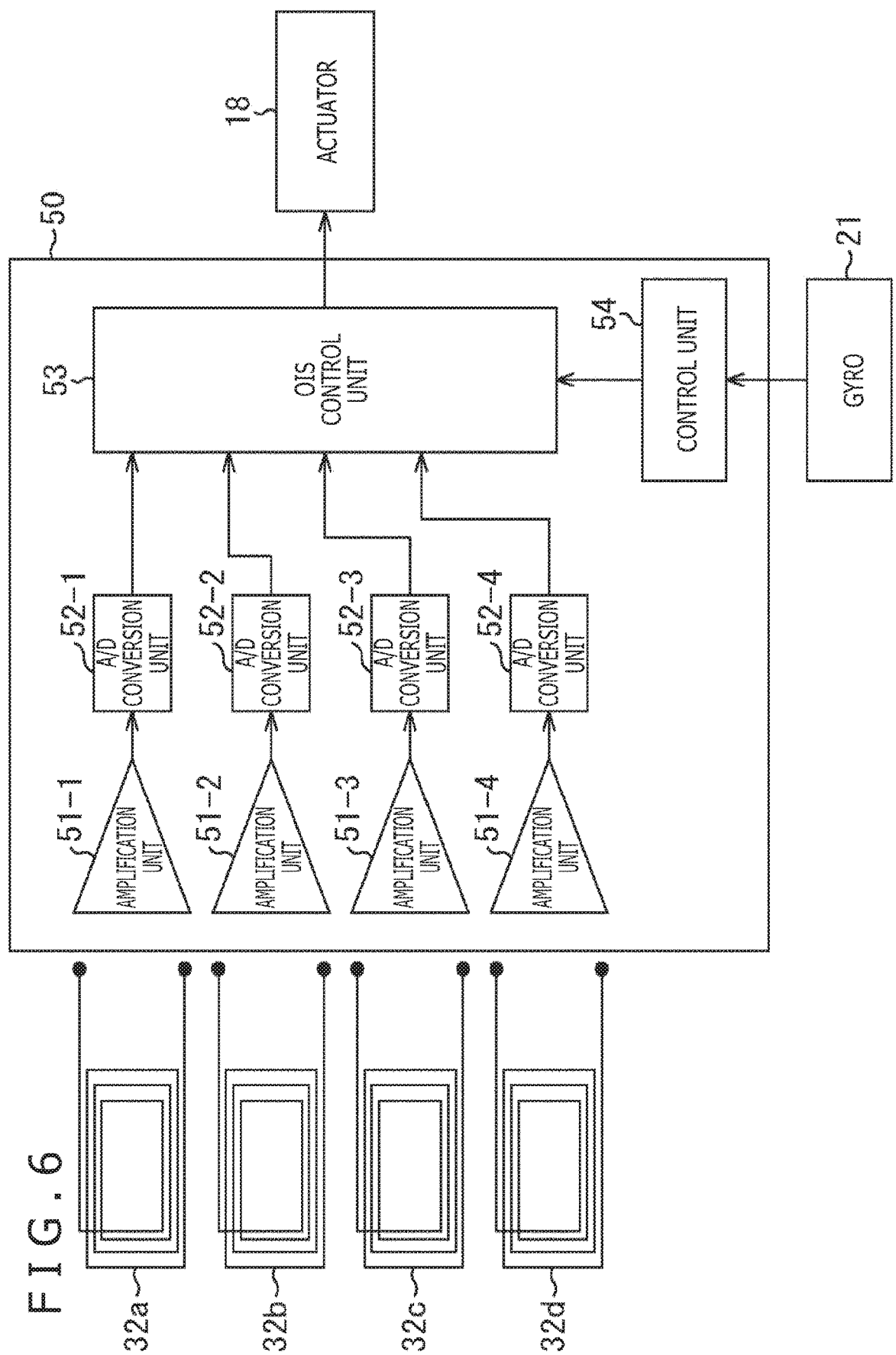
FIG. 6 is a diagram depicting a configuration example of a detection circuit.

FIG. 6 is a diagram depicting a configuration example of the detection circuit 50. Induced electromotive force generated in each of the position detection coils 32a to 33d is input to amplification units 51-1 to 51-4 of the detection circuit 50 to be amplified, respectively. The amplified induced electromotive force is input to corresponding A/D (Analog/Digital) conversion units 52-1 to 52-4 to convert analog data into digital data. The amplification units 51-1 to 51-4 will be hereinafter simply referred to as amplification units 51 in a case of no necessity of distinction between these units. Other parts will be described in a similar manner.

An OIS control unit 53 is a part controlling the actuator 18. The OIS control unit 53 recognizes an X-Y distance of the lens 16 (FIG. 1) on the basis of digital data received from the A/D conversion units 52-2 to 52-4. In a case of determination that correction in the X-Y direction is needed, i.e., in a case of determination that a shift in the X-Y direction is needed as image stabilization on the basis of sensing of hand-vibration by the gyro sensor 21, a PWM control signal corresponding to an X-Y shift distance needed for the correction is generated and supplied to the actuator 18.

Note that the OIS control unit 53 also performs processing for generating a PWM control signal according to a signal generated from a control unit 54 which controls image stabilization (OIS), and supplying the generated signal to the actuator 18. Moreover, as described below, a position of the lens 16 in the Z-axis direction is also detectable by using data associated with the position detection coils 32a to 32d. Accordingly, the OIS control unit 53 is also allowed to have a configuration for controlling auto focus (AF).

The detection circuit 50 may be provided inside the imaging device 1a as one integrated circuit, or may be provided outside the imaging device 1a. Moreover, the detection circuit 50 may be implemented as software instead of an integrated circuit, and may be implemented as software of an integrating CPU of a camera.

According to the present technology, there are provided a function of detecting induced electromotive force, and a function of highly accurately adjusting a focus of a lens and X-Y positions of the lens on the basis of the induced electromotive force. The scope of the present invention includes not only a case where these functions are implemented by an integrated circuit or software as described above, but also a case where these functions are implemented by other methods.

As described above, the positions of the lens 16 in the X-axis direction and the Y-axis direction are detectable by detecting induced electromotive force flowing in the position detection coils 32. This detection is achievable because a relation presented in FIG. 7 holds.

Figure 7:
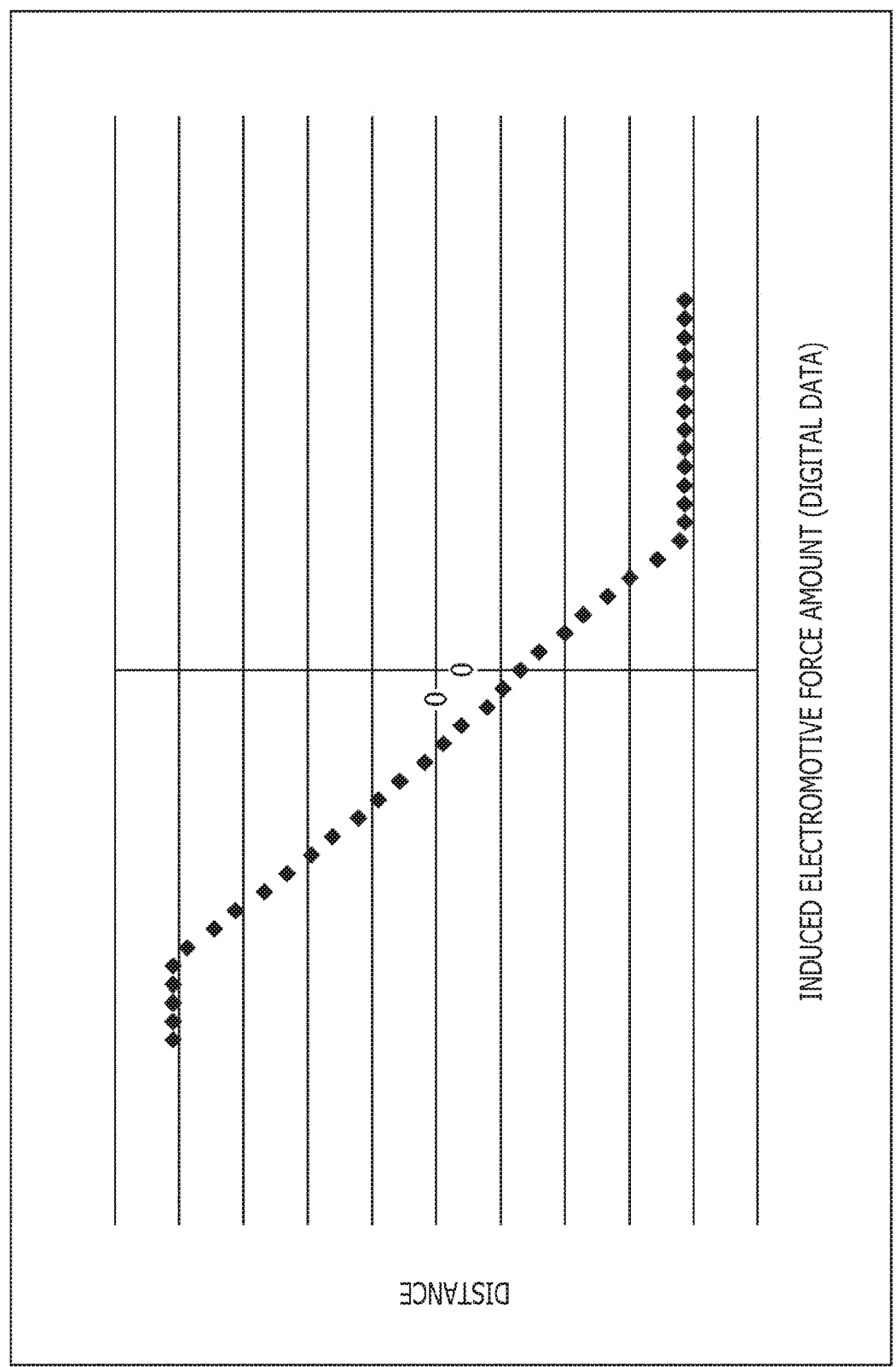
FIG. 7 is a diagram explaining a position of a lens and induced electromotive force.

FIG. 7 is a graph representing a relation between a position of the lens 16 and detected induced electromotive force. In FIG. 7, a vertical axis represents a position of the lens, while a horizontal axis represents a current amount of induced electromotive force (digital data).

For example, suppose that the lens 16 (lens holder 34) shifts in the X-axis direction by an effect of disturbance. In this case, the position detection coil 32a attached to the OIS holder 35 including the lens holder 34 also shifts in the X-axis direction. For example, a positional relation between the position detection coil 32a and the FP coil 31a is considered by way of example. When the position detection coil 32a shifts in the X-axis direction, the positional relation between the position detection coil 32a and the FP coil 31a, i.e., a distance between the position detection coil 32a and the FP coil 31a also changes.

For example, in a case of a large effect of disturbance, deviation of the lens 16 from the normal position increases. Accordingly, deviation of the lens holder 34 holding the lens 16, and the position detection coil 32a provided on the bottom surface of the OIS holder 35 including the lens holder 34 also increases. This deviation corresponds to the distance between the position detection coil 32a and the FP coil a.

An effect of the magnetic field generated by current flowing in the FP coil 31a on the position detection coil 32a increases in a state where the lens 16 (FP coil 31) is located close to the position detection coil 32a, and decreases in a state where the FP coil 31a is located away from the position detection coil 32a. Accordingly, induced electromotive force increases in the state where the FP coil 31a is located close to the position detection coil 32a, and decreases in the state where the FP coil 31a is located away from the position detection coil 32a.

The graph of FIG. 7 represents this point. FIG. 7 is a graph which expresses a case where the position detection coil 32a comes closer to the FP coil 31a in a direction from the upper side to the lower side in the figure. In addition, in the graph of FIG. 7, a current value increases in a direction from the left side to the right side in the figure. In the graph presented in FIG. 7, the vertical axis represents the distance between the position detection coil 32a and the FP coil a. Moreover, in FIG. 7, the distance is set to 0 when the position detection coil 32a and the FP coil 31a are located at normal positions. A current value has a positive value in a case of a flow in a predetermined direction, and has a negative value in a case of a flow in a direction opposite to the predetermined direction.

As apparent from the graph presented in FIG. 7, the induced electromotive force varies in a manner of a linear function. In view of the foregoing points, it is understood that a one-to-one relation holds between the induced electromotive force and the distance between the position detection coil 32a and the FP coil 31a. The position detection coil 32a moves with the lens holder 34, while the lens holder 85 holds the lens 16. Accordingly, the state that "the one-to-one relation holds between the induced electromotive force and the distance between the position detection coil 32a and the FP coil 31a" can be considered as a state that a one-to-one relation holds between the induced electromotive force and the position of the lens 16.

Accordingly, by detecting the induced electromotive force flowing in the position detection coil 32, the position of the lens 16 at that time is detectable.

By utilizing these relations, the detection circuit 50 is capable of detecting a position B which is a position of the lens 16 reached after control for shifting the lens 16 to a desired position A using the OIS control unit 53, for example.

Moreover, in a case of the presence of deviation between the desired position A and the detected position B, a shift to the desired position A is achievable with correction of this deviation. Accordingly, a high-performance lens shift is realizable.

Figure 8:
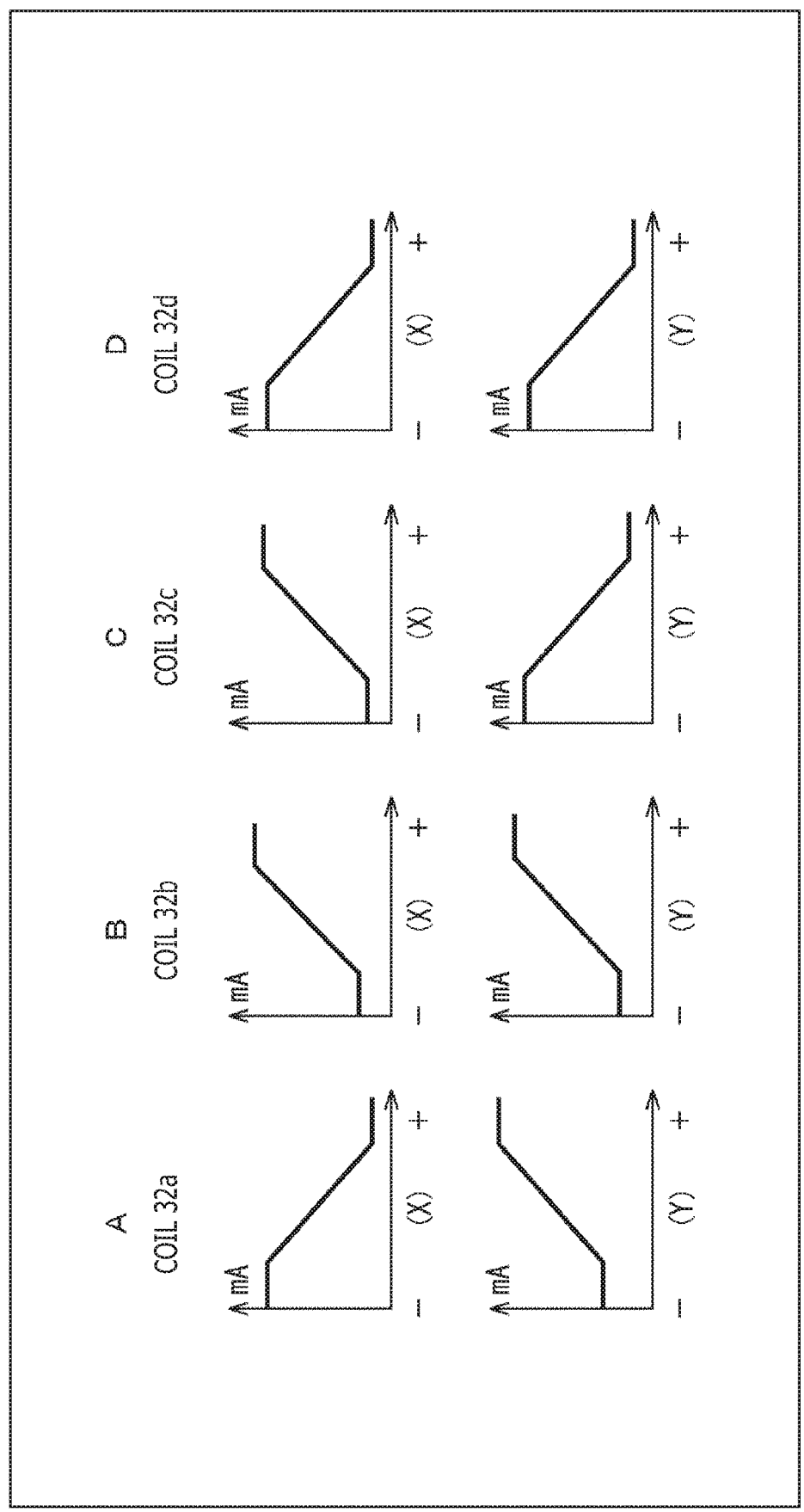
FIG. 8 illustrates diagrams explaining dielectric electromotive force generated in the position detection coils.

Description concerning detection of the position of the lens 16 in the X-Y plane will further continue. FIG. 8 is a diagram presenting a transition of induced electromotive force produced by a shift of the lens 16 in the X-Y direction by image stabilization for each of the position detection coils 32a to 33d.

The description continues while presenting an example of a case where each positional relation between the FP coils 31a to 31d and the position detection coils 32a to 32d corresponds to the relation presented in FIG. 4. Moreover, while not presented in FIG. 4, the lens 16 is located at a center portion of the board 41. For example, description that the lens 16 shifts in the +X direction in the following description refers to shifts of the position detection coils 32a to 32d similarly in the +X direction with the shift of the lens 16 in the +X direction.

Each of graphs presented in FIG. 8 is a graph obtained on an assumption that a horizontal direction corresponds to the X-axis direction, that a vertical direction corresponds to the Y-axis direction, and that the center of the lens 16 corresponds to 0 in FIG. 4. In this case, a left side corresponds to a negative direction (−X direction), while a right side corresponds to a positive direction (+X direction). In addition, an upper side corresponds to a positive direction (+Y direction), while a lower side corresponds to a negative direction (−Y direction).

When magnetic fields are generated from the FP coils 31 according to supply of current in the FP coils 31 by image stabilization, a large effect of the magnetic fields is imposed on the position detection coils 32 in a case where the lens 16 (position detection coils 32) is located close to the FP coils 31. On the other hand, a small effect of the magnetic fields is imposed on the position detection coils 32 in a case where the lens 16 (position detection coils 32) is located away from the FP coils 31.

This point is represented by graphs in parts A to D of FIG. 8. In each of the graphs presented in parts A to D of FIG. 8, a horizontal axis represents a position of the lens 16 (position detection coils 32), while a vertical axis represents induced electromotive force generated in the position detection coils 32. In addition, in each of parts A to D of FIG. 8, the graphs presented in an upper stage are graphs of dielectric electromotive force at the time of a shift of the lens 16 from the −X side to the +X side, while the graphs presented in a lower stage are graphs of dielectric electromotive force at the time of a shift of the lens 16 from the −Y side to the +Y side.

Referring to A of FIG. 8, in a case of a shift of the lens 16 from the −X side to the +X side, the state of the position detection coil 32a changes from a position close to the FP coil 31a to a position away from the FP coil 31a. In a case where this change is produced, the dielectric electromotive force generated in the position detection coil 32a gradually decreases with the shift of the lens 16 form the −X side to the +X side as presented in the upper graph in part A of FIG. 8.

On the other hand, in a case of a shift of the lens 16 from the −Y side to the +Y side, the state of the position detection coil 32a changes from a position away from the FP coil 31a to a position close to the FP coil 31a. In a case where this change is produced, the dielectric electromotive force generated in the position detection coil 32a gradually increases with the shift of the lens 16 form the −Y side to the +Y side as presented in the lower graph in part A of FIG. 8.

Referring to B of FIG. 8, in a case of a shift of the lens 16 from the −X side to the +X side, the state of the position detection coil 32b changes from a position away from the FP coil 31b to a position close to the FP coil 31b. In a case where this change is produced, the dielectric electromotive force generated in the position detection coil 32b gradually increases with the shift of the lens 16 form the −X side to the +X side as presented in the upper graph in part B of FIG. 8.

On the other hand, in a case of a shift of the lens 16 from the −Y side to the +Y side, the state of the position detection coil 32b changes from a position away from the FP coil 31b to a position close to the FP coil 31b. In a case where this change is produced, the dielectric electromotive force generated in the position detection coil 32b gradually increases with the shift of the lens 16 form the −Y side to the +Y side as presented in the lower graph in part B of FIG. 8.

Referring to C of FIG. 8, in a case of a shift of the lens 16 from the −X side to the +X side, the state of the position detection coil 32c changes from a position away from the FP coil 31c to a position close to the FP coil 31c. In a case where this change is produced, the dielectric electromotive force generated in the position detection coil 32c gradually increases with the shift of the lens 16 form the −X side to the +X side as presented in the upper graph in part C of FIG. 8.

On the other hand, in a case of a shift of the lens 16 from the −Y side to the +Y side, the state of the position detection coil 32c changes from a position close to the FP coil 31c to a position away from the FP coil 31c. In a case where this change is produced, the dielectric electromotive force generated in the position detection coil 32c gradually decreases with the shift of the lens 16 form the −Y side to the +Y side as presented in the upper graph in part C of FIG. 8.

Referring to D of FIG. 8, in a case of a shift of the lens 16 from the −X side to the +X side, the state of the position detection coil 32d changes from a position close to the FP coil 31d to a position away from the FP coil 31d. In a case where this change is produced, the dielectric electromotive force generated in the position detection coil 32d gradually decreases with the shift of the lens 16 form the −X side to the +X side as presented in the upper graph in part D of FIG. 8.

On the other hand, in a case of a shift of the lens 16 from the −Y side to the +Y side, the state of the position detection coil 32d changes from a position close to the FP coil 31d to a position away from the FP coil 31d. In a case where this change is produced, the dielectric electromotive force generated in the position detection coil 32d gradually decreases with the shift of the lens 16 form the −Y side to the +Y side as presented in the upper graph in part D of FIG. 8.

By utilizing these relations, the detection circuit 50 is capable of detecting the position B which is a position of the lens 16 reached after control for shifting the lens 16 to a desired position A using the OIS control unit 53, for example.

Moreover, in a case of the presence of deviation between the desired position A and the detected position B, the lens 16 can be shifted to the desired position A with correction of this deviation. Accordingly, a high-performance lens shift is achievable.

Second Embodiment

As described with reference to FIG. 8, the positions of the lens 16 in the X-axis direction and the Y-axis direction are detectable by measuring dielectric electromotive force generated in each of the position detection coils 32a to 32d. The positions of the lens 16 in the X-axis direction and the Y-axis direction are also detectable using only the two position detection coils 32 of the four position detection coils 32a to 32d.

Figure 9:
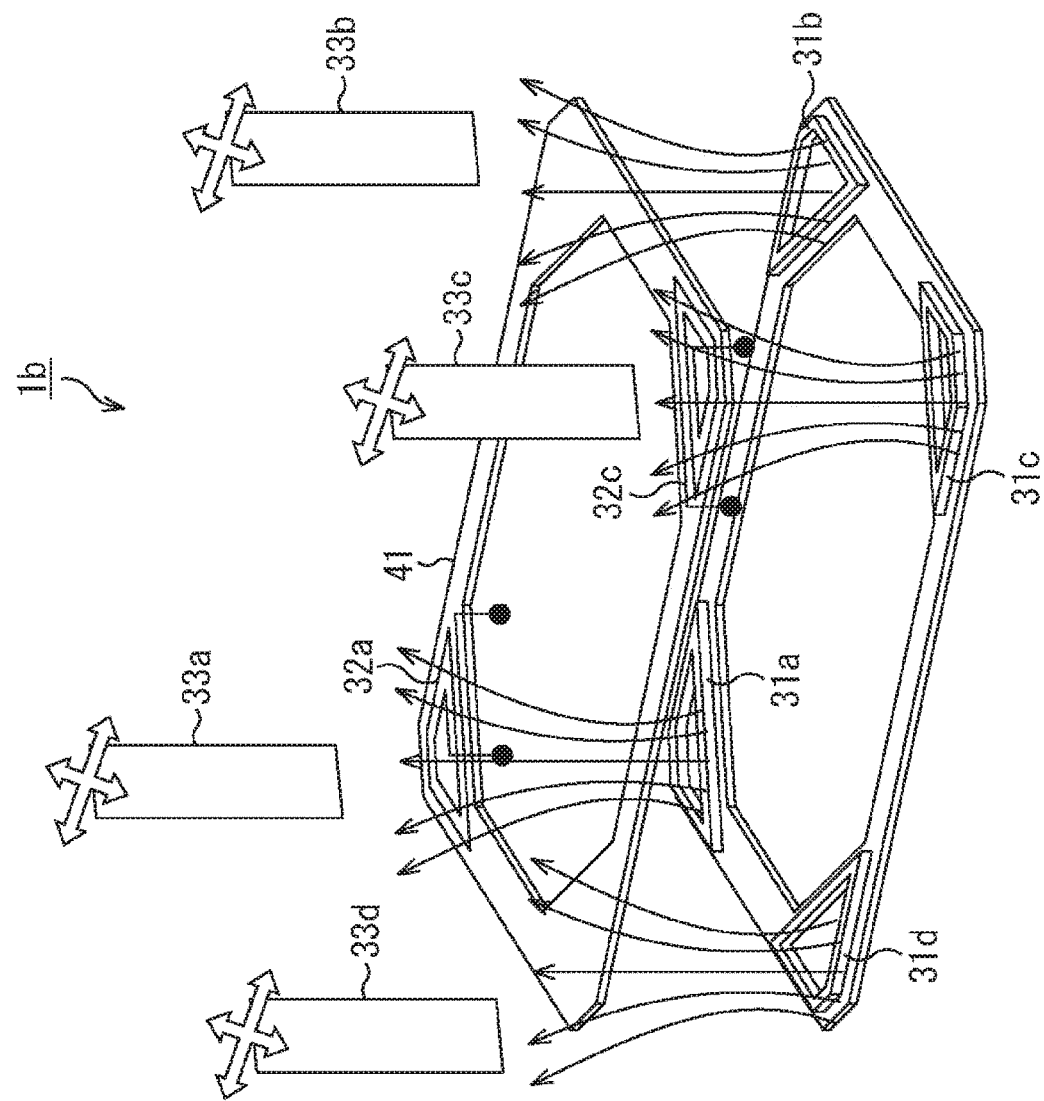
FIG. 9 is a diagram depicting another configuration example of the imaging device.

FIG. 9 depicts a configuration of an imaging device 1b including the two position detection coils 32. The imaging device 1b depicted in FIG. 9 has a configuration including the position detection coil 32a and the position detection coil 32c for detecting the positions of the lens 16 in the X-axis direction and the Y-axis direction.

Figure 10:
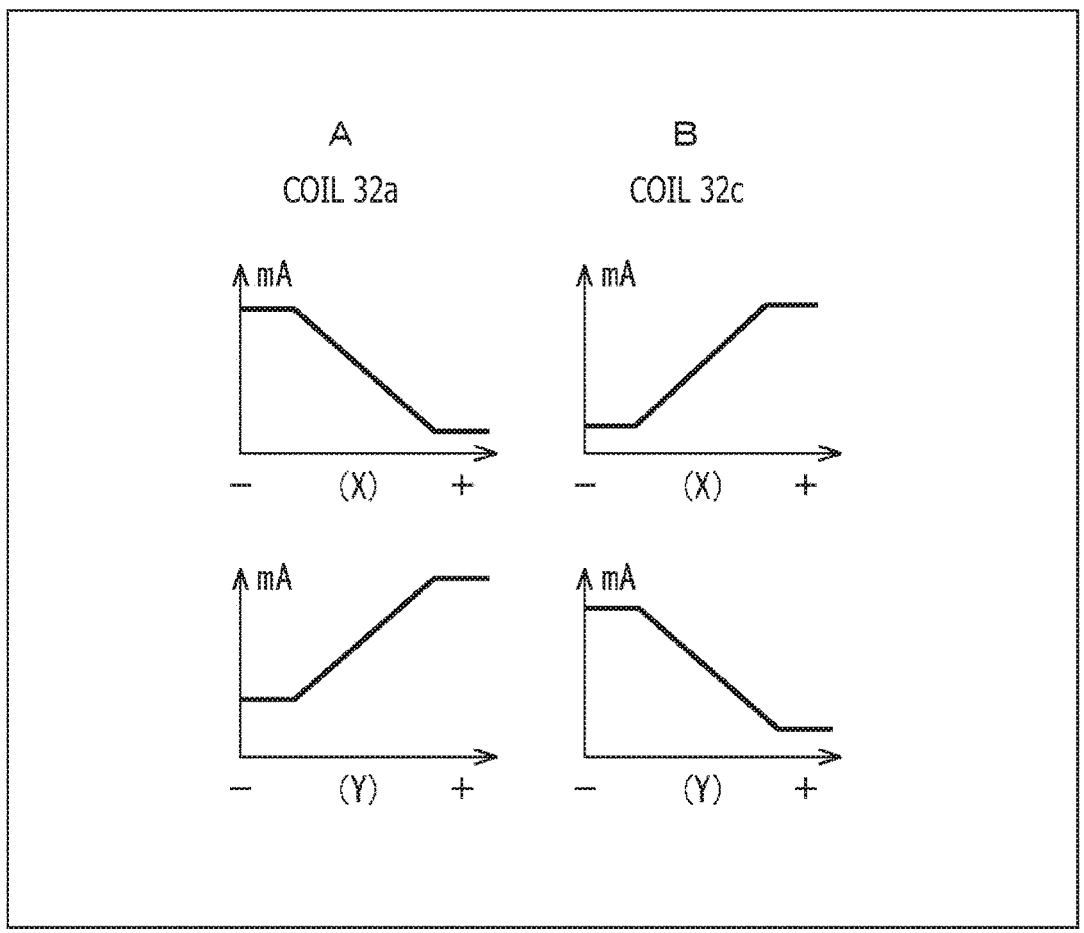
FIG. 10 illustrates diagrams explaining dielectric electromotive force generated in the position detection coils.

In a case of the imaging device 1b depicted in FIG. 9, the positions of the lens 16 in the X-axis direction and the Y-axis direction are detectable by measuring dielectric electromotive force generated in the position detection coil 32a and dielectric electromotive force generated in the position detection coil 32c as depicted in FIG. 10.

Specifically, as depicted in part A of FIG. 10, in a case where the lens 16 shifts from the −X side to the +X side, dielectric electromotive force generated in the position detection coil 32a gradually decreases with a shift of the lens from the −X side to the +X side. Accordingly, the position of the lens 16 in the X-axis direction is detectable by utilizing this point. Moreover, as depicted in part A of FIG. 10, in a case where the lens 16 shifts from the −Y side to the +Y side, dielectric electromotive force generated in the position detection coil 32a gradually increases with a shift of the lens from the −Y side to the +Y side. Accordingly, the position of the lens 16 in the Y-axis direction is detectable by utilizing this point.

As depicted in part B of FIG. 10, in a case where the lens 16 shifts from the −X side to the +X side, dielectric electromotive force generated in the position detection coil 32c gradually increases with a shift of the lens from the −X side to the +X side. Accordingly, the position of the lens 16 in the X-axis direction is detectable by utilizing this point. Moreover, as depicted in part B of FIG. 10, in a case where the lens 16 shifts from the −Y side to the +Y side, dielectric electromotive force generated in the position detection coil 32c gradually decreases with a shift of the lens from the −Y side to the +Y side. Accordingly, the position of the lens 16 in the Y-axis direction is detectable by utilizing this point.

For example, the position of the lens 16 in the X-axis direction is detectable from a measurement result of the induced electromotive force generated in the coil 32a, while the position of the lens 16 in the Y-axis direction is detectable from a measurement result of the induced electromotive force generated in the coil 32c.

Note that the example presented here is a case where the position detection coil 32a and the position detection coil 32c are provided, a configuration including the position detection coil 32a and the position detection coil 32d, a configuration including the position detection coil 32b and the position detection coil 32c, or a configuration including the position detection coil 32b and the position detection coil 32d may be adopted.

As the configuration of the imaging device 1 detecting the position of the lens 16 in the X-Y plane, either a configuration including the position detection coils 32 at four corners as depicted in FIG. 3 or a configuration including the position detection coils 32 at two corners as depicted in FIG. 9 may be adopted.

As depicted in FIG. 3, in a case of adoption of the position detection coils 32 provided at the four corners, the graphs of dielectric electromotive force presented in part A of FIG. 8 can be obtained from the position detection coil 32a, and the graphs of dielectric electromotive force presented in part B of FIG. 8 can be obtained from the position detection coil 32b, for example. In this case, two pieces of position information for detecting the position of the lens 16 in the X-axis direction or the Y-axis direction can be obtained.

On the basis of these two pieces of position information, the positions of the lens 16 in the X-axis direction and the Y-axis direction are detectable from a result of predetermined calculations, such as multiplication of two pieces of position information (values of induced electromotive force), addition of the two values, and subtraction to obtain an absolute value of a difference of the two values.

Even in a case where dielectric electromotive force generated in the one position detection coil 32 is small, position detection accuracy can be raised by adopting the configuration including the position detection coils 32 at four corners, and using a detection result of dielectric electromotive force of the position detection coils 32 provided at different two corners.

In the case of adoption of the configuration including the position detection coils 32 at two corners as depicted in FIG. 9, position detection accuracy may become lower than position detection accuracy in a case of adoption of the configuration including the position detection coils 32 at four corners. However, adoption of the configuration including the position detection coils 32 at two corners can offer advantageous effects such as more cost reduction than in the case of adoption of the position detection coils 32 at four corners, and miniaturization of the device achieved by providing other members at corners where the position detection coils 32 are not disposed.

Moreover, lowering of position detection accuracy is also avoidable by increasing the number of windings of each of the position detection coils 32, or adoption of a configuration which provides the position detection coils 32 at closest possible positions to the FP coils 31. Furthermore, needless to say, for separate use of the configurations depending on situations, the imaging device 1 not requiring highly accurate position detection may adopt the configuration including the position detection coils 32 at two corners, while the imaging device 1 requiring highly accurate position detection may adopt the configuration including the position detection coils 32 at four corners.

<Detection of Lens Inclination>

Detection of the two positions of the lens 16 in the X-axis direction and the Y-axis direction has been described in the above embodiment by way of example. Inclination of the lens 16 is also detectable on the basis of this detection.

Described above is an example assuming that the lens 16 is not inclined, i.e., the lens 16 and the imaging element 11 maintain a state parallel to each other. However, there is a possibility that the lens 16 (lens holder 34) comes into an inclined state. A function of detecting and correcting inclination at the time of inclination of the lens 16 is allowed to be provided.

In an ideal state of the lens 16 and the imaging element 11, an optical axis passing through the lens 16 extends perpendicularly to the imaging element 11. However, when at least one of the lens 16, the actuator 18, or the imaging element 11 is mounted with inclination, or comes into an inclined state during use, the optical axis passing through the lens 16 and the imaging element 11 may be brought into a state not perpendicular to each other.

Accordingly, described hereinafter will be a configuration also capable of detecting inclination of the lens 16 or the imaging element 11 by utilizing induced electromotive force generated in the position detection coils 32 described above.

Figure 11:
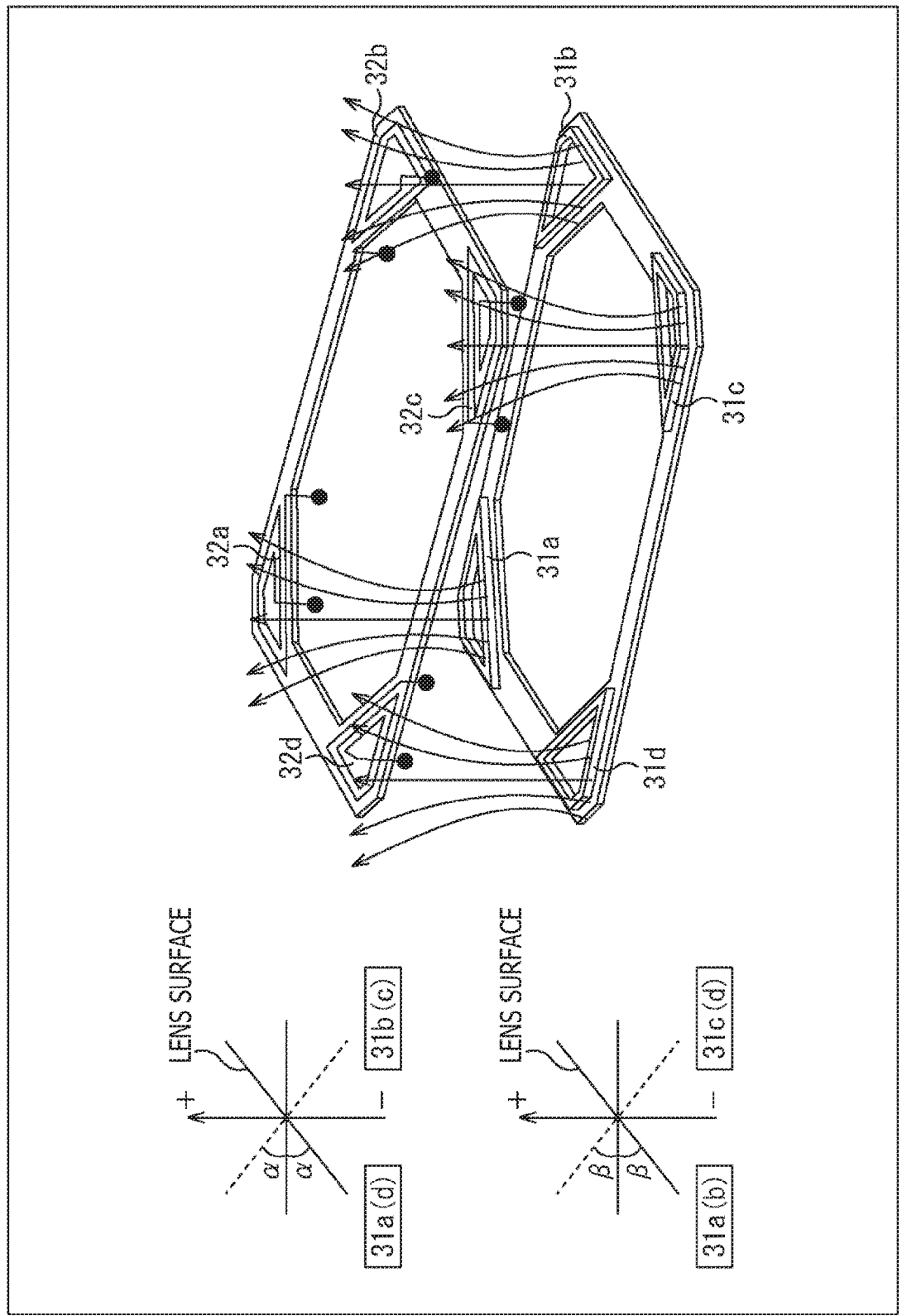
FIG. 11 is a diagram explaining detection of inclination.

FIG. 11 is a diagram schematically depicting an inclined state of the lens 16 in a configuration similar to the configuration of the imaging device 1a depicted in FIG. 3 (the part driving the lens 16 constituting the imaging device 1a). The state depicted in FIG. 11 is an example of a case where inclination is produced, i.e., the left side of the lens 16 (the board 41 on which the position detection coils 32 are provided) is located on the upper side, while the right side is located on the lower side in the figure.

In the situation depicted in FIG. 11, the FP coil 31a is positioned away from the position detection coil 32a, while the FP coil 31b is positioned close to the position detection coil 32b. In the case of this situation, therefore, induced electromotive force generated in the position detection coil 32a is smaller than induced electromotive force generated in the position detection coil 32b.

Similarly, in the situation depicted in FIG. 11, the FP coil 31d is positioned away from the position detection coil 32d, while the FP coil 31c is positioned close to the position detection coil 32c. In the case of this situation, therefore, induced electromotive force generated in the position detection coil 32d is smaller than induced electromotive force generated in the position detection coil 32c.

Dielectric electromotive force generated in each of the position detection coils 32 thus differs depending on the relative positions of the FP coils 31 and the position detection coils 32 similar to the case described above, such as the case described with reference to FIG. 8.

Inclination $\alpha$ and inclination $\beta$ of the lens 16 are established here as depicted in a left part of FIG. 11. With respect to the FP coil 31a and the FP coil 31b (X-axis direction), the inclination $\alpha$ has a negative value in a state where the lens 16 is inclined toward the side close to the FP coil 31a, and has a positive value in a state where the lens 16 is inclined toward the side close to the FP coil 31b. In other words, an angle formed by the imaging surface of the imaging element 11 and a line segment connecting the position detection coil 32a and the position detection coil 32b is the inclination $\alpha$.

The inclination α has a negative value in a state where the line segment connecting the position detection coil 32a and the position detection coil 32b is inclined toward the side close to the FP coil 31a, and has a positive value in a state where the line segment is inclined toward the side close to the FP coil 31b.

In addition, with respect to the FP coil 31a and the FP coil 31d (Y-axis direction), the inclination β has a negative value in a state where the lens 16 is inclined toward the side close to the FP coil 31a, and has a positive value in a state where the lens 16 is inclined toward the side close to the FP coil 31d. In other words, an angle formed by the imaging surface of the imaging element 11 and a line segment connecting the position detection coil 32a and the position detection coil 32d is the inclination D. The inclination β has a negative value in a state where the line segment connecting the position detection coil 32a and the position detection coil 32d is inclined toward the side close to the FP coil 31a, and has a positive value in a state where the line segment is inclined toward the side close to the FP coil 31d.

Figure 12:
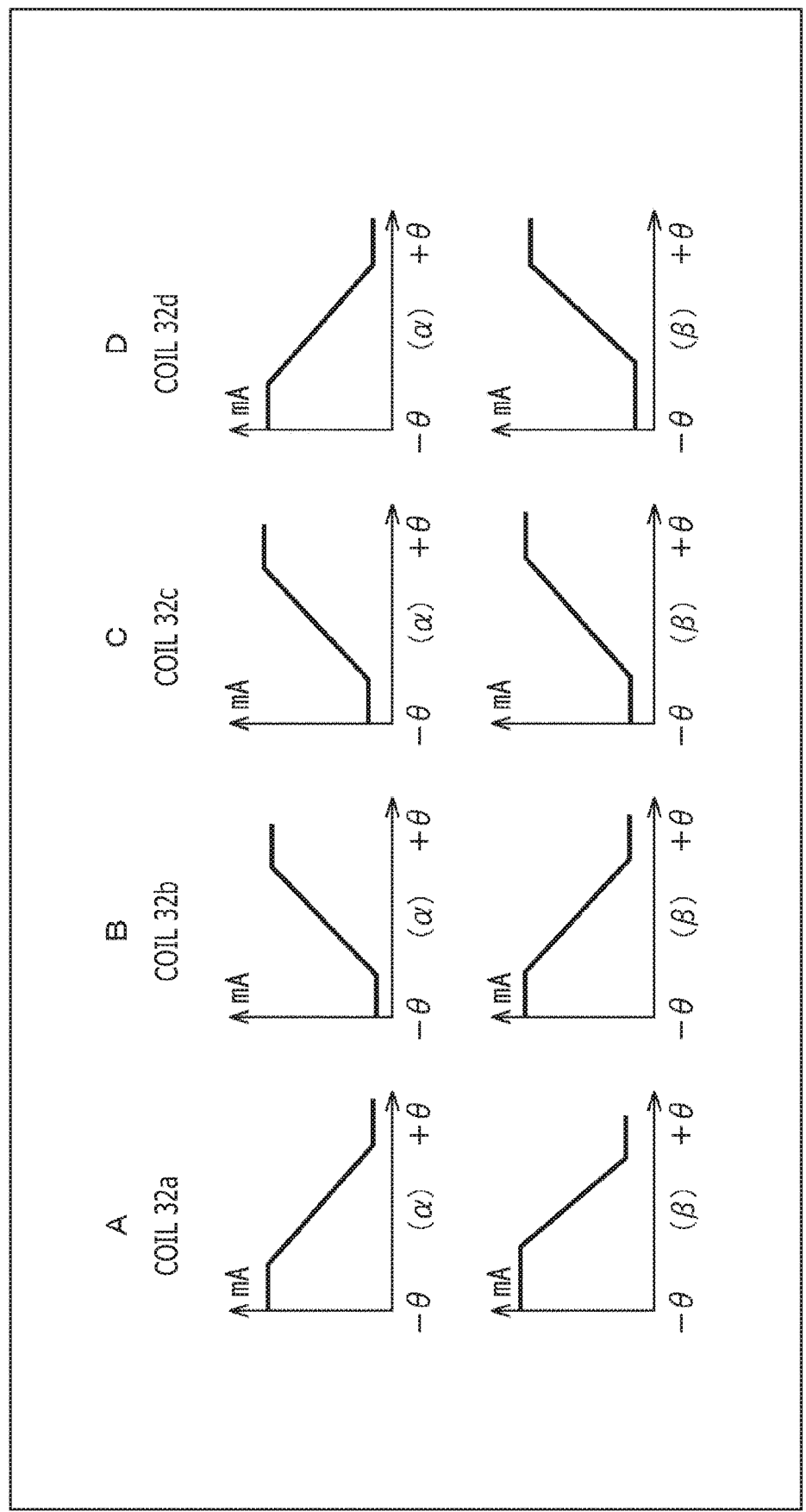
FIG. 12 illustrates diagrams explaining dielectric electromotive force generated in the position detection coils.

FIG. 12 presents a distribution of induced electromotive force in the presence of inclination. Referring to a graph of dielectric electromotive force of the position detection coil 32a presented in part A of FIG. 12, dielectric electromotive force decreases in a case where the inclination α changes from negative θ to positive θ, i.e., in a case where the position detection coil 32a is inclined in a direction away from the FP coil 31a. In addition, referring to a graph of dielectric electromotive force of the position detection coil 32a presented in part A of FIG. 12, dielectric electromotive force decreases in a case where the inclination β changes from negative θ to positive θ, i.e., in a case where the position detection coil 32a is inclined in a direction away from the FP coil 31a.

Referring to a graph of dielectric electromotive force of the position detection coil 32b presented in part B of FIG. 12, dielectric electromotive force increases in a case where the inclination α changes from negative θ to positive θ, i.e., in a case where the position detection coil 32b is inclined in a direction toward the FP coil 31b. In addition, referring to a graph of dielectric electromotive force of the position detection coil 32b presented in part B of FIG. 12, dielectric electromotive force decreases in a case where the inclination R changes from negative θ to positive θ, i.e., in a case where the position detection coil 32b is inclined in a direction away from the FP coil 31b.

Referring to a graph of dielectric electromotive force of the position detection coil 32c presented in part C of FIG. 12, dielectric electromotive force increases in a case where the inclination α changes from negative θ to positive θ, i.e., in a case where the position detection coil 32c is inclined in a direction toward the FP coil 31c. In addition, referring to a graph of dielectric electromotive force of the position detection coil 32c presented in part C of FIG. 12, dielectric electromotive force increases in a case where the inclination β changes from negative θ to positive θ, i.e., in a case where the position detection coil 32c is inclined in a direction toward the FP coil 31c.

Referring to a graph of dielectric electromotive force of the position detection coil 32d presented in part D of FIG. 12, dielectric electromotive force decreases in a case where the inclination α changes from negative θ to positive θ, i.e., in a case where the position detection coil 32d is inclined in a direction away from the FP coil 31d. In addition, referring to a graph of dielectric electromotive force of the position detection coil 32d presented in part D of FIG. 12, dielectric electromotive force increases in a case where the inclination β changes from negative θ to positive θ, i.e., in a case where the position detection coil 32d is inclined in a direction toward the FP coil 31d.

As apparent from above, induced electromotive force generated in the position detection coils 32 differs from each other depending on the inclination of the lens 16 (a difference in the positional relation between the FP coils 31 and the position detection coils 32). This point is same to the corresponding point described with reference to FIG. 8.

For example, on an assumption that dielectric electromotive force in the absence of inclination of the lens 16 in the X-axis direction (at the time of inclination α=0) is a reference (reference value), the absence of inclination in the X-axis direction can be determined if an absolute value of a difference between the dielectric electromotive force of the position detection coil 32a and the reference value is equal to an absolute value of a difference between the dielectric electromotive force of the position detection coil 32b and the reference value. If the absolute values of these differences are not equal to each other, the presence of inclination in the X-axis direction can be determined.

Moreover, in a case of determination that inclination is present as a result of the determination, the position of the FP coil 31 for the position detection coil 32a and the position of the FP coil 31 for the position detection coil 32b are obtained on the basis of intensity of dielectric electromotive force, and the inclination α can be calculated from a positional relation between the obtained positions. Furthermore, when the inclination α is calculated, a correction amount sufficient for cancelling the inclination α can be calculated for correction of the inclination based on the correction amount.

While the method for detecting the inclination of the lens 16 using the two position detection coils 32 disposed in the X-axis direction has been presented by way of example, the inclination may be detected by other methods (calculations). In addition, while the combination of the position detection coil 32a and the position detection coil 32b has been presented as the two position detection coils 32 disposed in the X-axis direction in the above example, the two position detection coils 32 may be a combination of the position detection coil 32c and the position detection coil 32d, a combination of the position detection coil 32a and the position detection coil 32c, and a combination of the position detection coil 32b and the position detection coil 32d.

Similarly, as for inclination in the Y-axis direction, detection and correction of inclination in the Y-axis direction are achievable on the basis of dielectric electromotive force of each of the position detection coil 32a and the position detection coil 32d. In addition, a combination other than the combination of the position detection coil 32a and the position detection coil 32d, such as a combination of the position detection coil 32a and the position detection coil 32c, a combination of the position detection coil 32b and the position detection coil 32d, and a combination of the position detection coil 32b and the position detection coil 32c may be adopted.

According to the present technology, therefore, each of the positions of the lens 16 in the X-axis direction, the Y-axis direction, and the Z-axis direction, and the inclination of the lens 16 is detectable. Accordingly, not only correction in the X-Y direction, but also tilt-correction is achievable as image stabilization. As a result, the imaging device 1 with higher functionality is obtainable.

Moreover, when inclination is detected by executing inclination detection to which the present technology is applied during manufacture of the imaging device 1, this inclination can be corrected. In a case where the inclination is predetermined inclination or greater, the imaging device 1 can be removed from a manufacturing line. It is therefore apparent that a defect of deviation of the optical axis improves by a performance test executed after manufacture. Accordingly, reduction of manufacturing costs is achievable.

Third Embodiment

Each of the imaging devices 1a and 1b described above by way of example is a case where the position detection coils 32 are provided to detect positions in the X-Y direction. A position of the lens 16 in the Z-axis direction is also detectable utilizing dielectric electromotive force generated in the position detection coils 32. The description continues while presenting an imaging device 1c as the imaging device 1 capable of also detecting the position of the lens 16 in the Z-axis direction.

Figure 13:
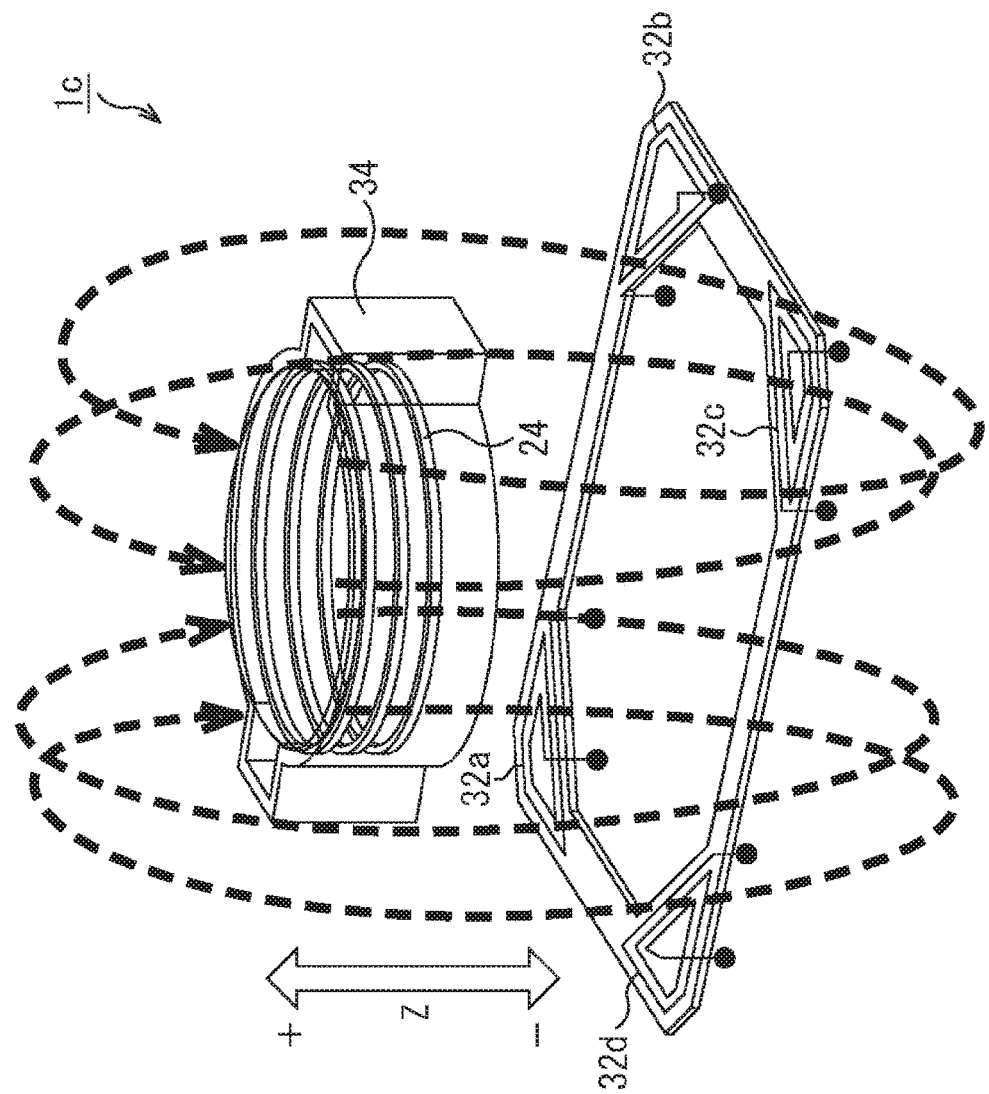
FIG. 13 is a diagram depicting still another configuration example of the imaging device.

FIG. 13 is a diagram for explaining magnetic fields generated by a PWM waveform, and induced electromotive force generated by the magnetic fields. When current flows in the coil 24 formed on the side surface of the lens holder 34, force is generated in an up-down direction in the figure. The lens 16 held by the lens holder 34 (the lens 16 held by the lens holder 34) shifts upward or downward by the generated force. As a result, the distance between the lens 16 and the imaging element 11 changes. Auto focus (AF: Auto-Focus) is achieved by this mechanism.

A magnetic field generated in the coil 24 reaches the position detection coils 32. As a result, dielectric electromotive force is produced in the position detection coils 32 by the magnetic field generated in the coil 24. In this case, the dielectric electromotive force decreases in a state where the coil 24 is located away from the position detection coils 32, and increases in a state where the coil 24 is located close to the position detection coil 32 similarly to above.

The Z position of the lens 16 is detectable by measuring dielectric electromotive force generated in each of the position detection coils 32a to 32d, and integrating the measured values. As depicted in FIG. 13, it is assumed that a position of the lens 16 on the upper side in the figure (direction away from the not-depicted imaging element 11) is positive, and that a position on the lower side in the figure (direction toward the not-depicted imaging element 11) is a negative direction.

Figure 14:
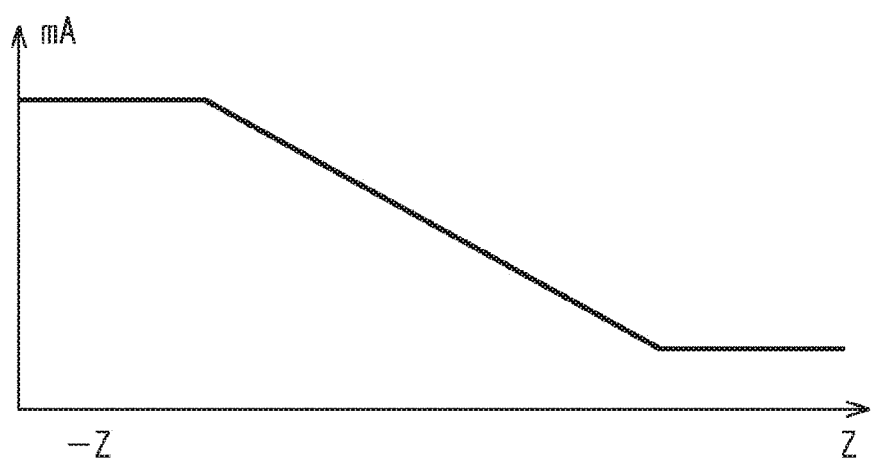
FIG. 14 is a diagram explaining dielectric electromotive force generated in the position detection coils.

FIG. 14 is a diagram presenting a change of a value obtained by integrating the induced electromotive force generated in each of the position detection coils 32a to 32d in a case where the lens 16 (coil 24) shifts from the −Z side to the +Z side, i.e., when the state of the lens 16 changes from a position close to the position detection coils 32a to 32d to a position away from the position detection coils 32a to 32d. As depicted in FIG. 14, dielectric electromotive force gradually decreases with a shift of the lens 16 (coil 24) from −Z side to the +Z side.

When the lens 16 (the coil 24) shifts in the Z-axis direction, the lens 16 moves away from or closer to the position detection coils 32a to 32d. Accordingly, the change of dielectric electromotive force generated in the position detection coils 32a to 32d as depicted in FIG. 14 is equivalent to a change of the distance of the position detection coils 32 from the FP coils 31 as described above.

In this manner, the position of the lens 16 in the Z-axis direction is detectable by measuring dielectric electromotive force generated in each of the position detection coils 32a to 32d.

Fourth Embodiment

Figure 15:
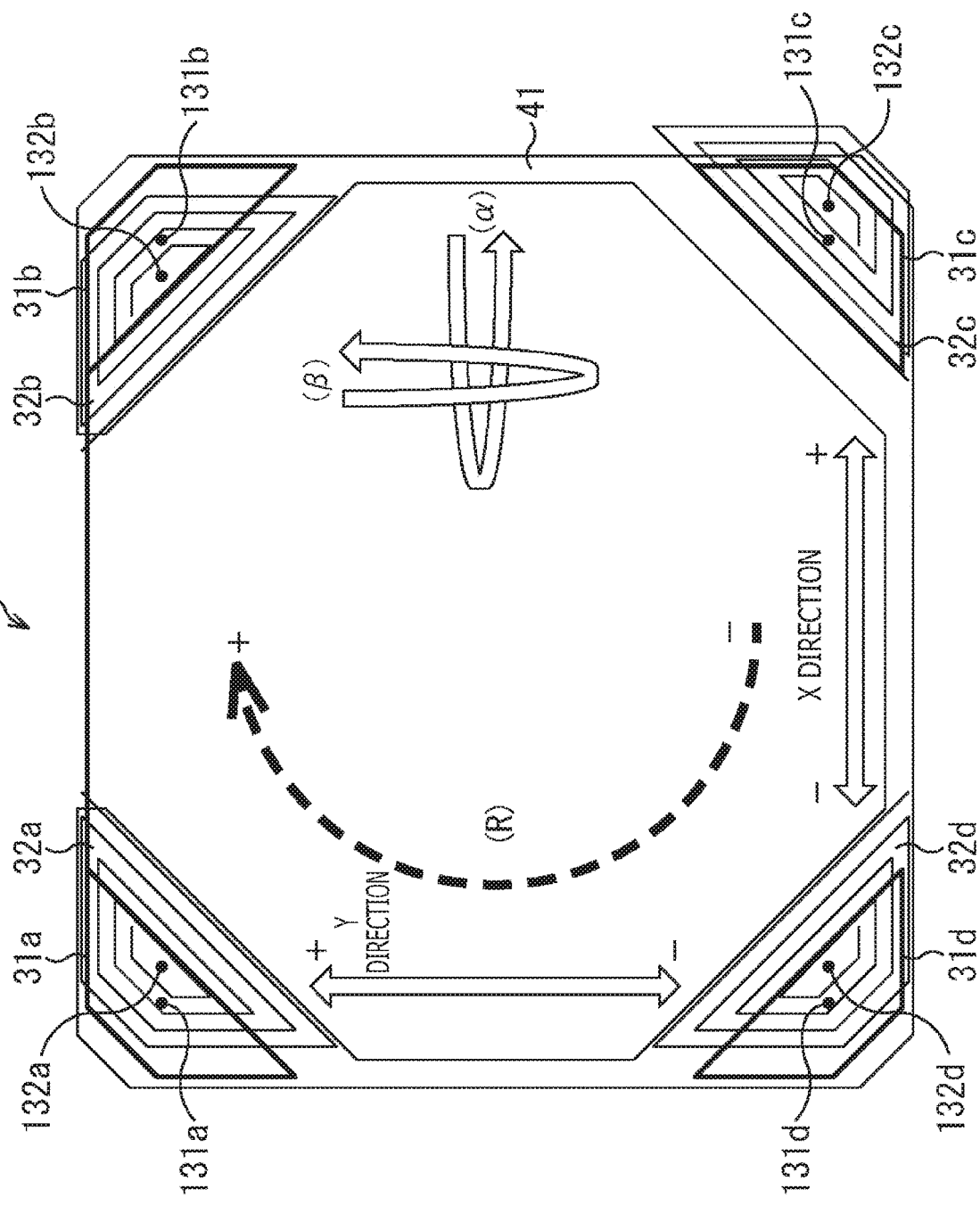
FIG. 15 is a diagram depicting yet another configuration example of the imaging device.

As described in the first and second embodiments, the positions of the lens 16 in the X-axis direction and the Y-axis direction are detectable by using the position detection coils 32 as depicted in FIG. 15. Moreover, inclination (tilt) of the lens 16, i.e., the angles α and β are also detectable. Furthermore, as described in the third embodiment, the position of the lens 16 in the Z-axis direction is detectable by using the position detection coils 32.

In addition, a position of rotation is also detectable. In FIG. 15, rotation is indicated as (R). The description continues while presenting an imaging device 1d as the imaging device 1 capable of also detecting the position of the lens 16 in a rotation direction in this manner.

Rotation is positional deviation of the lens 16 produced by rotation of the lens 16. As depicted in FIG. 15, the description continues here on an assumption that a direction of upward rotation of the lens 16 in the figure is a positive direction, and that a direction of downward rotation in the figure is a negative direction.

The positions of the lens 16 are detectable in the directions of the six axes, i.e., the X-axis direction, the Y-axis direction, the Z-axis direction, the tilt angle α, the tilt angle β, and the rotation by measuring dielectric electromotive force generated in each of the position detection coils 32.

In a case where the position of the lens 16 is detected in each of the directions of six axes in this manner, the respective position detection coils 32a to 32d are preferably arranged in such positions as to obtain different graphs of dielectric electromotive force for each of the six axes. An example of this arrangement is therefore presented in FIG. 15.

The center positions of the FP coils 31 and the center positions of the corresponding position detection coil 32 are configured to deviate from each other. This arrangement allows the position detection coils 32 to efficiently receive magnetic fields from the FP coils 31 even when the FP coils 31 and the position detection coils 32 deviate from the normal positions as described with reference to FIG. 4.

The deviation directions of the centers of the FP coil 31 and the centers of the position detection coil 32 may be designed to be equalized for each combination of the FP coils 31 and the position detection coils 32, or may be designed to be different directions.

Refer to FIG. 4 again. The center of the FP coil 31a and the center of the position detection coil 32a are located on a straight line extending toward the center of the board 41. The center of the position detection coil 32a is designed to be located inside the center of the FP coil 31a.

The center of the FP coil 31b and the center of the position detection coil 32b are located on a straight line extending toward the center of the board 41. The center of the position detection coil 32b is designed to be located inside the center of the FP coil 31b.

The center of the FP coil 31c and the center of the position detection coil 32c are located on a straight line extending toward the center of the board 41. The center of the position detection coil 32c is designed to be located inside the center of the FP coil 31c.

The center of the FP coil 31d and the center of the position detection coil 32d are located on a straight line extending toward the center of the board 41. The center of the position detection coil 32d is designed to be located inside the center of the FP coil 31d.

In this case, the center of the position detection coil 32d is designed to be subsequent to the center of the FP coil 31d in the direction toward the center of the board 41. In other words, the position detection coils 32 are designed to be located inside the FP coils 31.

In the case of this design, the graphs of the dielectric electromotive force of the position detection coils 32*a* to 32*d* become uniform when the positional relation (distance) between the FP coils 31 and the position detection coils 32 changes by rotation of the lens 16. In this case, the center of the position detection coil 32*a* shifts in a direction away from the center of the FP coil 31*a* by rotation in a direction from the negative side toward the positive side (a direction indicated by (R) in FIG. 15, and corresponds to a direction from the negative side toward the positive side in the Y direction in FIG. 4). Accordingly, induced electromotive force generated in the position detection coil 32*a* decreases.

In addition, the center of the position detection coil 32*b* shifts in a direction away from the center of the FP coil 31*b*. Accordingly, induced electromotive force generated in the position detection coil 32*b* also decreases. Moreover, the center of the position detection coil 32*c* shifts in a direction away from the center of the FP coil 31*c*. Accordingly, induced electromotive force generated in the position detection coil 32*c* also decreases. Furthermore, the center of the position detection coil 32*d* shifts in a direction away from the center of the FP coil 31*d*. Accordingly, induced electromotive force generated in the position detection coil 32*d* also decreases.

In this case, therefore, dielectric electromotive force generated in each of the position detection coils 32*a* to 32*d* decreases, and the same graph is thus obtained for the position detection coils 32*a* to 32*d*. In addition, in a case where rotation of the lens 16 occurs in a direction from the positive side toward the negative side, the center of each of the position detection coils 32*a* to 32*d* shifts in a direction away from the center of the corresponding one of the FP coils 31*a* to 31*d*. Accordingly, induced electromotive force generated in the position detection coil 32*a* similarly decreases.

In a case where the same graph is obtained in this manner, detection of the rotation directions and the positions is difficult.

Different graphs can be obtained by adjusting the deviation direction for each combination of the FP coils 31 and the position detection coils 32. In addition, in a case of detection of the positions of the lens 16 in the six axes, it is preferable to obtain different graphs for each of the six axes. These graphs can also be obtained by adjusting the deviation direction of each combination of the FP coils 31 and the position detection coils 32.

FIG. 15 depicts an example of adjustment of the direction and the size of the deviation of each combination of the FP coils 31 and the position detection coils 32. The position detection coils 32 depicted in FIG. 15 are disposed at asymmetrical positions with respect to an optical center.

A center 131*a* of the FP coil 31*a* and a center 132*a* of the position detection coil 32*a* are located on a straight line extending in parallel to the X axis of the board 41. The center 132*a* of the position detection coil 32*a* is designed to be located inside the center 131*a* of the FP coil 31*a*. In other words, the position detection coil 32*a* is disposed at a position on the upper right side with respect to a line as a reference connecting the center 131*a* of the FP coil 31*a* and the center of the board 41.

A center 131*b* of the FP coil 31*b* and a center 132*b* of the position detection coil 32*b* are located on a straight line extending in parallel to the X axis of the board 41. The center 132*b* of the position detection coil 32*b* is designed to be located inside the center 131*b* of the FP coil 31*b*. In other words, the position detection coil 32*b* is disposed at a position on the upper left side with respect to a line as a reference connecting the center 131*b* of the FP coil 31*b* and the center of the board 41.

A center 131*c* of the FP coil 31*c* and a center 132*c* of the position detection coil 32*c* are located on a straight line extending in parallel to the X axis of the board 41. The center 132*c* of the position detection coil 32*c* is designed to be located outside the center 131*c* of the FP coil 31*c*. In other words, the position detection coil 32*c* is disposed at a position on the upper right side with respect to a line as a reference connecting the center 131*c* of the FP coil 31*c* and the center of the board 41.

A center 131*d* of the FP coil 31*d* and a center 132*d* of the position detection coil 32*d* are located on a straight line extending in parallel to a side of the board 41 in the X-axis direction. The center 132*d* of the position detection coil 32*d* is designed to be located inside the center 131*d* of the FP coil 31*d*. In other words, the position detection coil 32*d* is disposed at a position on the lower right side with respect to a line as a reference connecting the center 131*d* of the FP coil 31*d* and the center of the board 41.

According to the example depicted in FIG. 15, each of the position detection coil 32*a*, the position detection coil 32*b*, and the position detection coil 32*d* is disposed inside the paired FP coil 31, while the position detection coil 32*c* is disposed outside the FP coil 31*c*.

In a case where induced electromotive force is measured in each of the position detection coils 32*a* to 32*d* disposed in this manner, graphs different from the graphs described above are contained. Accordingly, description will continue while presenting a list of the graphs in FIG. 16. The graphs presented in FIG. 16 each indicate a change of dielectric electromotive force generated in the position detection coils 32 for each of six axes.

Figure 16:
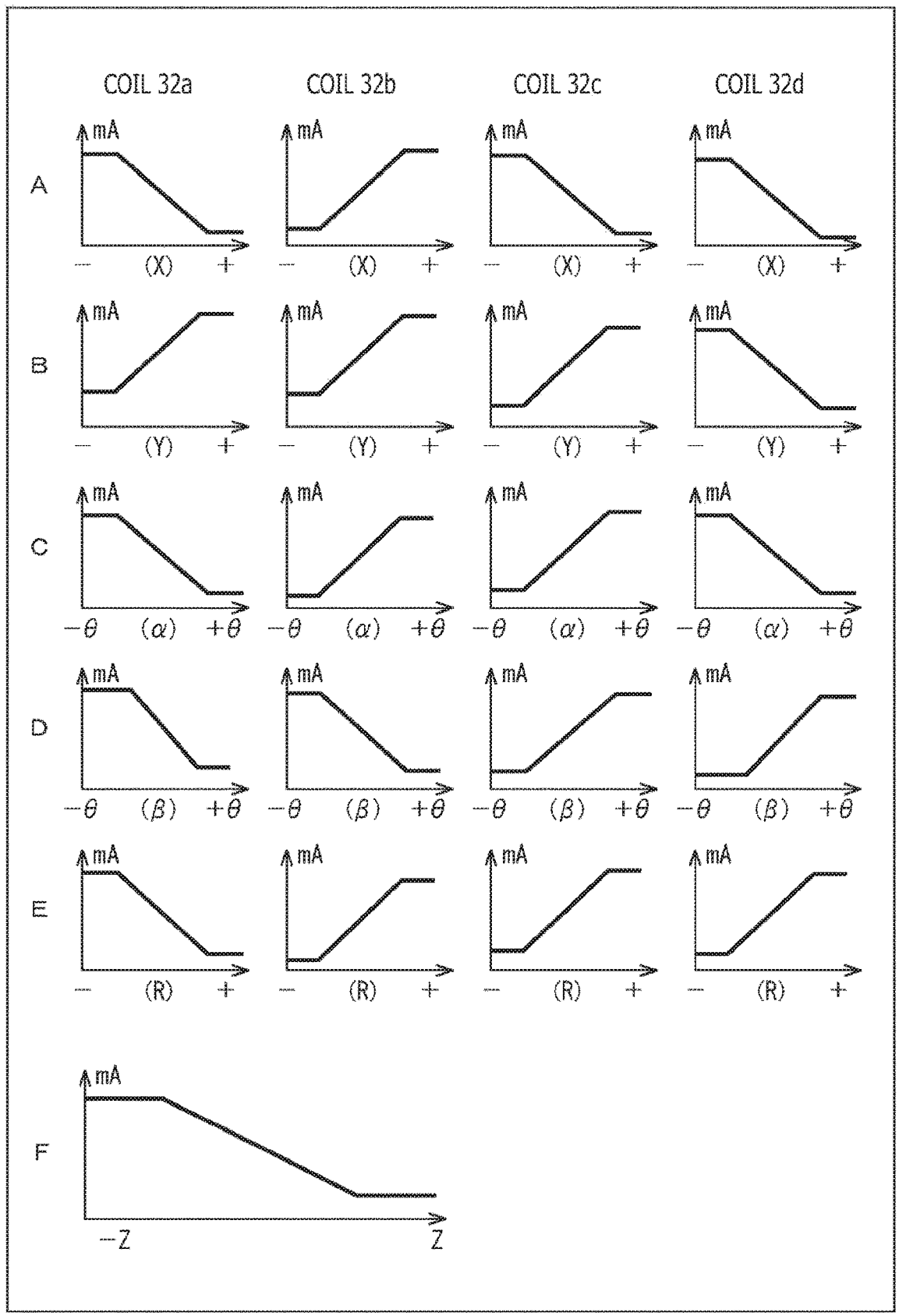
FIG. 16 illustrates diagrams explaining dielectric electromotive force generated in the position detection coils.

Graphs in part A of FIG. 16 are graphs obtained by measuring dielectric electromotive force generated in each of the position detection coils 32*a* to 32*d* when the lens 16 shifts from the negative side to the positive side in the X-axis direction.

Referring to part A of FIG. 16, in a case of a shift of the lens 16 from the −X side to the +X side, the state of the position detection coil 32*a* changes from a position close to the FP coil 31*a* to a position away from the FP coil 31*a*. Accordingly, the dielectric electromotive force generated in the position detection coil 32*a* gradually decreases with the shift of the lens 16 from the −X side to the +X side.

Moreover, in a case of a shift of the lens 16 from the −X side to the +X side, the state of the position detection coil 32*b* changes from a position away from the FP coil 31*b* to a position close to the FP coil 31*b*. Accordingly, the dielectric electromotive force generated in the position detection coil 32*b* gradually increases with the shift of the lens 16 from the −X side to the +X side.

Furthermore, in a case of a shift of the lens 16 from the −X side to the +X side, the state of the position detection coil 32*c* changes from a position close to the FP coil 31*c* to a position away from the FP coil 31*c*. Accordingly, the dielectric electromotive force generated in the position detection coil 32*c* gradually decreases with the shift of the lens 16 from the −X side to the +X side.

In addition, in a case of a shift of the lens 16 from the −X side to the +X side, the state of the position detection coil 32*d* changes from a position close to the FP coil 31*d* to a position away from the FP coil 31*d*. Accordingly, the dielectric electromotive force generated in the position detection coil 32*d* gradually decreases with the shift of the lens 16 from the −X side to the +X side.

Graphs in part B of FIG. 16 are graphs obtained by measuring dielectric electromotive force generated in each of the position detection coils 32*a* to 32*d* when the lens 16 shifts from the negative side to the positive side in the Y-axis direction.

Referring to part B of FIG. 16, in a case of a shift of the lens 16 from the −Y side to the +Y side, the state of the position detection coil 32*a* changes from a position away from the FP coil 31*a* to a position close to the FP coil 31*a*. Accordingly, the dielectric electromotive force generated in the position detection coil 32*a* gradually increases with the shift of the lens 16 from the −Y side to the +Y side.

Moreover, in a case of a shift of the lens 16 from the −Y side to the +Y side, the state of the position detection coil 32*b* changes from a position away from the FP coil 31*b* to a position close to the FP coil 31*b*. Accordingly, the dielectric electromotive force generated in the position detection coil 32*b* gradually increases with the shift of the lens 16 from the −Y side to the +Y side.

Furthermore, in a case of a shift of the lens 16 from the −Y side to the +Y side, the state of the position detection coil 32*c* changes from a position away from the FP coil 31*c* to a position close to the FP coil 31*c*. Accordingly, the dielectric electromotive force generated in the position detection coil 32*c* gradually increases with the shift of the lens 16 from the −Y side to the +Y side.

In addition, in a case of a shift of the lens 16 from the −Y side to the +Y side, the state of the position detection coil 32*d* changes from a position close the FP coil 31*d* to a position away from the FP coil 31*d*. Accordingly, the dielectric electromotive force generated in the position detection coil 32*d* gradually decreases with the shift of the lens 16 from the −Y side to the +Y side.

Graphs in part C of FIG. 16 are graphs obtained by measuring dielectric electromotive force generated in each of the position detection coils 32*a* to 32*d* when the lens 16 shifts from the negative side to the positive side in the angle α direction.

In addition, graphs in part D of FIG. 16 are graphs obtained by measuring dielectric electromotive force generated in each of the position detection coils 32*a* to 32*d* when the lens 16 shifts from the negative side to the positive side in the angle R direction.

A change of induced electromotive force of the position detection coils 32 with a change of the inclination angle α and the angle β of the lens 16 is similar to the corresponding change in the case depicted in FIG. 12. Accordingly, the similar description of the change is omitted.

Graphs in part E of FIG. 16 are graphs obtained by measuring dielectric electromotive force generated in each of the position detection coils 32*a* to 32*d* when the lens 16 shifts from the negative side to the positive side in the rotation direction.

Referring to part E of FIG. 16, in a case of a shift of the lens 16 from the negative side to the positive side, the state of the position detection coil 32*a* changes from a position close to the FP coil 31*a* to a position away from the FP coil 31*a*. Accordingly, the dielectric electromotive force generated in the position detection coil 32*a* gradually decreases with the shift of the lens 16 from the negative side to the positive side.

Moreover, in a case of a shift of the lens 16 from the negative side to the positive side, the state of the position detection coil 32*b* changes from a position away from the FP coil 31*b* to a position close to the FP coil 31*b*. Accordingly, the dielectric electromotive force generated in the position detection coil 32*b* gradually increases with the shift of the lens 16 from the negative side to the positive side.

Furthermore, in a case of a shift of the lens 16 from the negative side to the positive side, the state of the position detection coil 32*c* changes from a position away from the FP coil 31*c* to a position close to the FP coil 31*c*. Accordingly, the dielectric electromotive force generated in the position detection coil 32*c* gradually increases with the shift of the lens 16 from the negative side to the positive side.

In addition, in a case of a shift of the lens 16 from the negative side to the positive side, the state of the position detection coil 32*d* changes from a position away from the FP coil 31*d* to a position close to the FP coil 31*d*. Accordingly, the dielectric electromotive force generated in the position detection coil 32*d* gradually increases with the shift of the lens 16 from the negative side to the positive side.

A graph in part F of FIG. 16 is a graph obtained by measuring dielectric electromotive force generated in each of the position detection coils 32*a* to 32*d* during a shift of the lens 16 from the negative side to the positive side in the Z-axis direction, and integrating the measured values.

A change of induced electromotive force of the position detection coils 32 with a shift of the lens 16 in the Z direction is similar to the corresponding change in the case depicted in FIG. 14. Accordingly, the similar description of the change is omitted.

As presented in FIG. 16, graphs in different patterns are obtained in each of the X-axis direction, the Y-axis direction, the angle α direction, the angle α direction, the rotation direction, and the Z-axis direction. In addition, there is no direction where the same graph is only obtained. Accordingly, a positional shift of the lens 16 in each of the directions of these six axes is detectable.

As described with reference to FIGS. 15 and 16, positional detection in each of image stabilization (X-axis and Y-axis directions), tilt (angles α and β), rotation, and auto focus (Z-axis direction) is achievable by adjusting the positional relation between the FP coils 31 and the position detection coils 32.

Note that the positional relation between the FP coils 31 and the position detection coils 32 is not limited to the positional relation presented in FIG. 15 by way of example.

Fifth Embodiment

Described above in the first through fourth embodiments is the case where the FP coils 31 are disposed on the actuator 18. However, the FP coils 31 may be disposed on a component other than the actuator 18.

Figure 17:
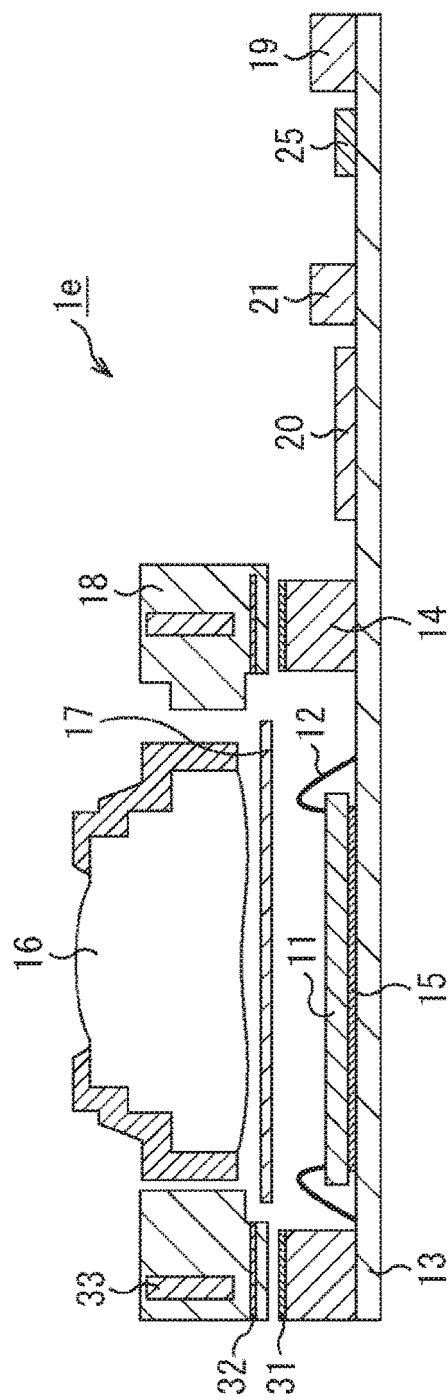
FIG. 17 is a diagram depicting a further configuration example of the imaging device.

FIG. 17 depicts a configuration example of an imaging device 1*e* which includes the FP coils 31 disposed on the spacer 14. According to the imaging device 1*e* depicted in FIG. 17, the FP coils 31 are disposed in a region on the spacer 14 and below the actuator 18. Other configurations are similar to the corresponding configurations of the imaging device 1*a* depicted in FIG. 1.

In such a manner, the FP coils 31 are provided in such a state as to face the magnets 33 in parallel to each other. Accordingly, the image stabilization function is achievable similarly to the above embodiments. Moreover, positional detection in the directions of the six axes is achievable by providing the position detection coils 32 between the FP coils 31 and the magnets 33 similar to the above embodiments.

Sixth Embodiment

Each of the imaging devices 1a to 1c has a similar basic configuration, and is different only in the parts equipped with the FP coils 31 and the position detection coils 32, and the number of the FP coils 31 and the position detection coils 32. These differences do not affect the configuration of the imaging device 1.

The imaging device 1 is allowed to have a uniform configuration regardless of the positions at which the FP coils 31 and the position detection coils 32 are provided, and the number of the FP coils 31 and the position detection coils 32. In other words, the present technology is applicable not only to the configurations of the imaging devices 1a to 1e described above, but also to any configuration of the imaging device 1.

Accordingly, other configurations of the imaging device 1 will be hereinafter described. However, similarly to above, the configuration of the imaging device 1 is not limited to the configurations described here only by way of example.

Figure 18:
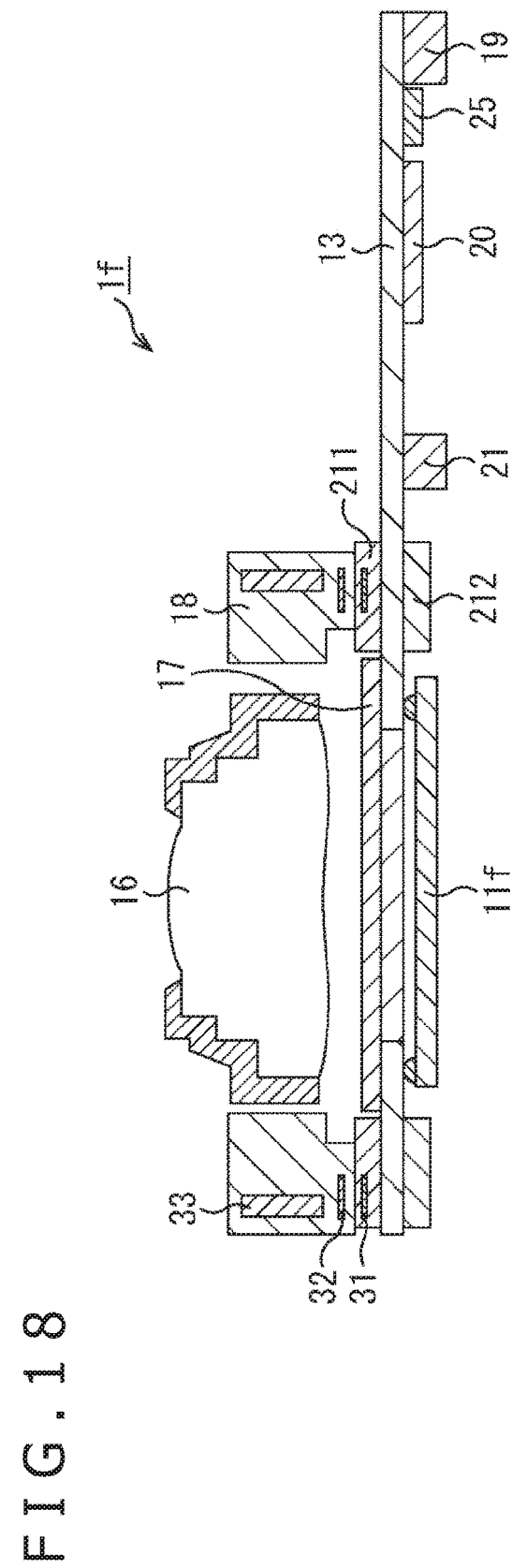
FIG. 18 is a diagram depicting a still further configuration example of the imaging device.

FIG. 18 is a diagram depicting another configuration example of the imaging device 1. An imaging device 1f depicted in FIG. 18 is the imaging device 1f which includes an imaging element 11f (e.g., the imaging element 11 of the imaging device 1a depicted in FIG. 1) having a flip chip structure as the imaging element 11.

According to the imaging device 1f depicted in FIG. 18, an electric signal output from the imaging element 11f is output to the outside via a holder 211 having a circuit function. The holder 211 also has a holder function for the actuator 18. The electric signal from the imaging element 11f is output to the outside via the circuit board 13 which is thin and connected to the holder 211.

Moreover, as depicted in FIG. 18, in a case where the imaging element 11f is provided below the circuit board 13 (on the side opposite to the lens 16), a protection member 212 is further provided to protect the imaging element 11f when the imaging device 1f is mounted on a terminal.

Even for the imaging device 1f thus configured, the FP coils 31 and the position detection coils 32 can be provided on the actuator 18, the spacer 14 (corresponding to the holder 211 in the case of the imaging device 1f), or the like. Accordingly, a structure detecting the positions of the lens 16 is obtainable.

Seventh Embodiment

Figure 19:
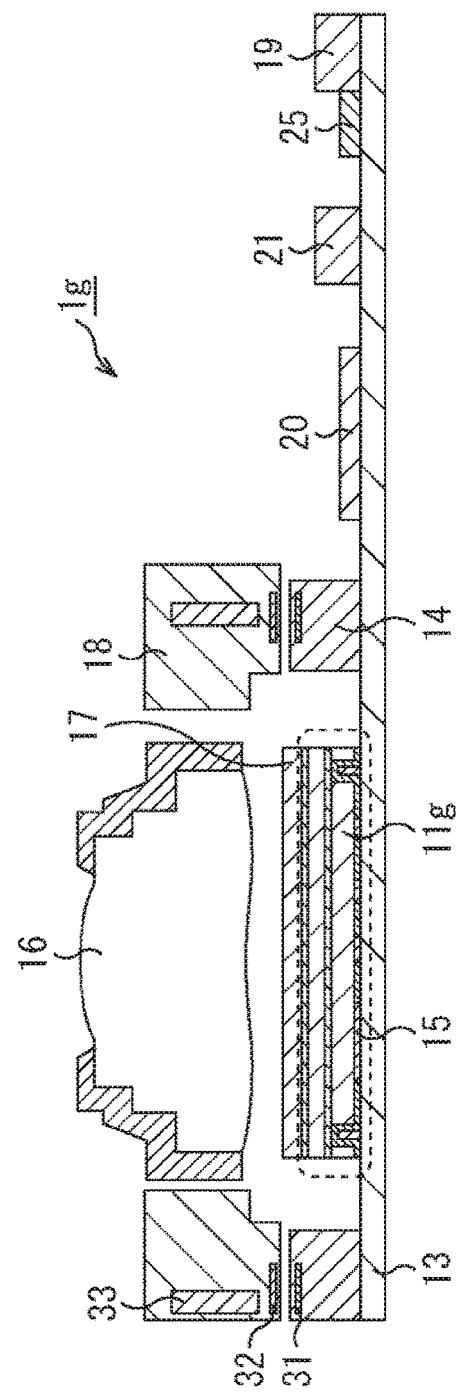
FIG. 19 is a diagram depicting a yet further configuration example of the imaging device.

FIG. 19 is a diagram depicting still another configuration example of the imaging device 1. An imaging device 1g depicted in FIG. 19 has a configuration which includes an imaging element 11g having a CSP (Chip size package) shape as the imaging element 11.

Even in the case where the imaging element 11g having a CSP shape is used as the imaging element 11, the FP coils 31 and the position detection coils 32 can be provided on the actuator 18, the spacer 14, or the like. Accordingly, a structure detecting the positions of the lens 16 is obtainable.

Eighth Embodiment

Figure 20:
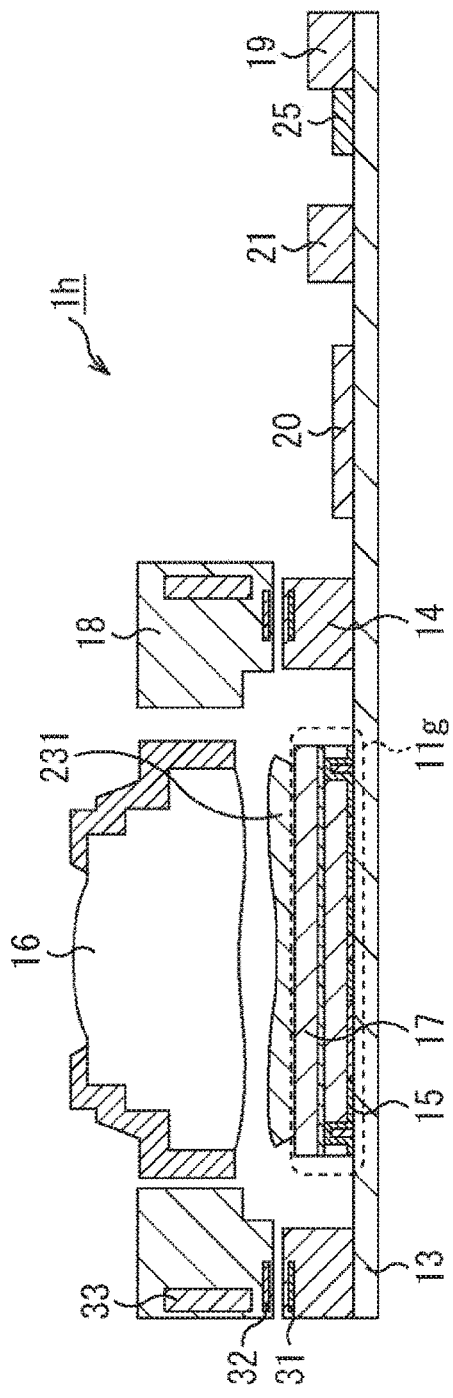
FIG. 20 is a diagram depicting a yet further configuration example of the imaging device.

FIG. 20 is a diagram depicting yet another configuration example of the imaging device 1. An imaging device 1h depicted in FIG. 20 has a configuration which includes the imaging element 11g having a CSP shape as the imaging element 11 similar to the imaging device 1g depicted in FIG. 19.

Further, according to the imaging device 1h depicted in FIG. 20, a glass substrate of an imaging element 1d having a CSP shape has a function (filter) for cutting infrared light. A lens 231 is provided on the glass substrate.

As described above, the glass substrate of the imaging element 11d has the function for cutting infrared light. In this case, a thickness of the infrared cut filter is allowed to decrease. Accordingly, reduction of a height of the imaging device 1h is achievable.

Further, the lens 231 is provided on the glass substrate. In other words, a lowermost layer lens in a plurality of lenses constituting the lens 16 is provided on the glass substrate of the imaging element 11g having a CSP shape. According to this configuration, the thickness of the imaging device 1h is allowed to further decrease.

Even for the imaging device 1h having a reduced thickness as described above, the FP coils 31 and the position detection coils 32 can be provided on the actuator 18, the spacer 14, or the like. Accordingly, a structure detecting the positions of the lens 16 is obtainable.

According to the present technology, improvement of performance and miniaturization of an imaging device are achievable by controlling positions of a lens focus, image stabilization, tilt, rotation, and the like of the imaging device.

The imaging device 1 described above is applicable to a digital video camera, a digital still camera, and the like. Further, the imaging device 1 described above is applicable to an image input camera such as a monitoring camera and a car-mounted camera. Furthermore, the imaging device 1 described above is applicable to an electronic apparatus such as a scanner device, a facsimile device, a videophone device, and a mobile terminal device equipped with a camera.

<Application Example to Endoscopic Surgery System>

The technology according to the present disclosure is applicable to various products. For example, the technology according to the present disclosure may be applied to an endoscopic surgery system.

Figure 21:
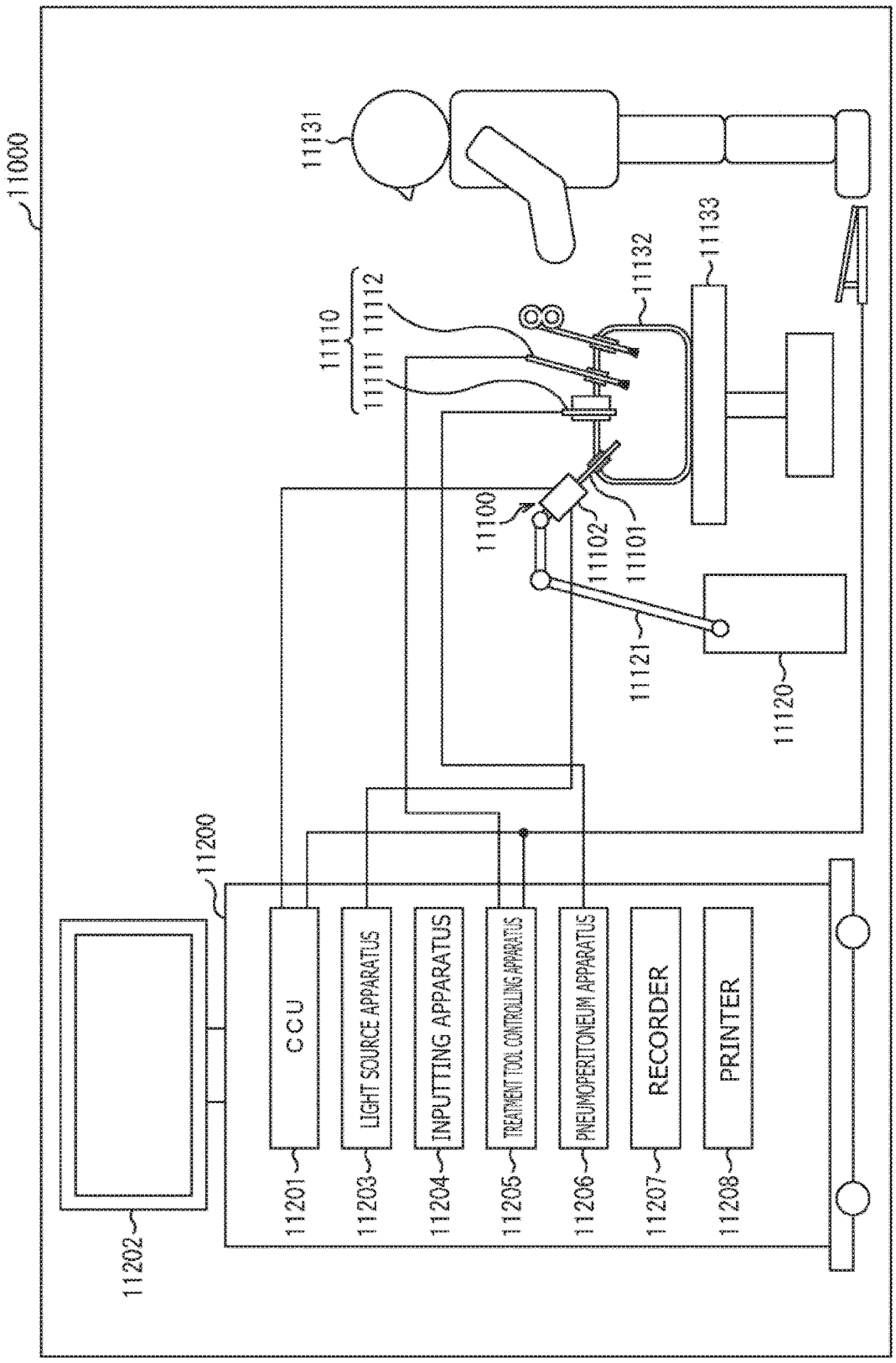
FIG. 21 is a view depicting an example of a schematic configuration of an endoscopic surgery system.

FIG. 21 is a view depicting an example of a schematic configuration of an endoscopic surgery system to which the technology according to an embodiment of the present disclosure (present technology) can be applied.

In FIG. 21, a state is illustrated in which a surgeon (medical doctor) 11131 is using an endoscopic surgery system 11000 to perform surgery for a patient 11132 on a patient bed 11133. As depicted, the endoscopic surgery system 11000 includes an endoscope 11100, other surgical tools 11110 such as a pneumoperitoneum tube 11111 and an energy device 11112, a supporting arm apparatus 11120 which supports the endoscope 11100 thereon, and a cart 11200 on which various apparatus for endoscopic surgery are mounted.

The endoscope 11100 includes a lens barrel 11101 having a region of a predetermined length from a distal end thereof to be inserted into a body cavity of the patient 11132, and a camera head 11102 connected to a proximal end of the lens barrel 11101. In the example depicted, the endoscope 11100 is depicted which includes as a rigid endoscope having the lens barrel 11101 of the hard type. However, the endoscope 11100 may otherwise be included as a flexible endoscope having the lens barrel 11101 of the flexible type.

The lens barrel 11101 has, at a distal end thereof, an opening in which an objective lens is fitted. A light source apparatus 11203 is connected to the endoscope 11100 such that light generated by the light source apparatus 11203 is introduced to a distal end of the lens barrel 11101 by a light guide extending in the inside of the lens barrel 11101 and is irradiated toward an observation target in a body cavity of the patient 11132 through the objective lens. It is to be noted that the endoscope 11100 may be a forward-viewing endoscope or may be an oblique-viewing endoscope or a side-viewing endoscope.

An optical system and an image pickup element are provided in the inside of the camera head 11102 such that reflected light (observation light) from the observation target is condensed on the image pickup element by the optical system. The observation light is photo-electrically converted by the image pickup element to generate an electric signal corresponding to the observation light, namely, an image signal corresponding to an observation image. The image signal is transmitted as RAW data to a CCU 11201.

The CCU 11201 includes a central processing unit (CPU), a graphics processing unit (GPU) or the like and integrally controls operation of the endoscope 11100 and a display apparatus 11202. Further, the CCU 11201 receives an image signal from the camera head 11102 and performs, for the image signal, various image processes for displaying an image based on the image signal such as, for example, a development process (demosaic process).

The display apparatus 11202 displays thereon an image based on an image signal, for which the image processes have been performed by the CCU 11201, under the control of the CCU 11201.

The light source apparatus 11203 includes a light source such as, for example, a light emitting diode (LED) and supplies irradiation light upon imaging of a surgical region to the endoscope 11100.

An inputting apparatus 11204 is an input interface for the endoscopic surgery system 11000. A user can perform inputting of various kinds of information or instruction inputting to the endoscopic surgery system 11000 through the inputting apparatus 11204. For example, the user would input an instruction or a like to change an image pickup condition (type of irradiation light, magnification, focal distance or the like) by the endoscope 11100.

A treatment tool controlling apparatus 11205 controls driving of the energy device 11112 for cautery or incision of a tissue, sealing of a blood vessel or the like. A pneumoperitoneum apparatus 11206 feeds gas into a body cavity of the patient 11132 through the pneumoperitoneum tube 11111 to inflate the body cavity in order to secure the field of view of the endoscope 11100 and secure the working space for the surgeon. A recorder 11207 is an apparatus capable of recording various kinds of information relating to surgery. A printer 11208 is an apparatus capable of printing various kinds of information relating to surgery in various forms such as a text, an image or a graph.

It is to be noted that the light source apparatus 11203 which supplies irradiation light when a surgical region is to be imaged to the endoscope 11100 may include a white light source which includes, for example, an LED, a laser light source or a combination of them. Where a white light source includes a combination of red, green, and blue (RGB) laser light sources, since the output intensity and the output timing can be controlled with a high degree of accuracy for each color (each wavelength), adjustment of the white balance of a picked up image can be performed by the light source apparatus 11203. Further, in this case, if laser beams from the respective RGB laser light sources are irradiated time-divisionally on an observation target and driving of the image pickup elements of the camera head 11102 are controlled in synchronism with the irradiation timings. Then images individually corresponding to the R, G and B colors can be also picked up time-divisionally. According to this method, a color image can be obtained even if color filters are not provided for the image pickup element.

Further, the light source apparatus 11203 may be controlled such that the intensity of light to be outputted is changed for each predetermined time. By controlling driving of the image pickup element of the camera head 11102 in synchronism with the timing of the change of the intensity of light to acquire images time-divisionally and synthesizing the images, an image of a high dynamic range free from underexposed blocked up shadows and overexposed highlights can be created.

Further, the light source apparatus 11203 may be configured to supply light of a predetermined wavelength band ready for special light observation. In special light observation, for example, by utilizing the wavelength dependency of absorption of light in a body tissue to irradiate light of a narrow band in comparison with irradiation light upon ordinary observation (namely, white light), narrow band observation (narrow band imaging) of imaging a predetermined tissue such as a blood vessel of a superficial portion of the mucous membrane or the like in a high contrast is performed. Alternatively, in special light observation, fluorescent observation for obtaining an image from fluorescent light generated by irradiation of excitation light may be performed. In fluorescent observation, it is possible to perform observation of fluorescent light from a body tissue by irradiating excitation light on the body tissue (autofluorescence observation) or to obtain a fluorescent light image by locally injecting a reagent such as indocyanine green (ICG) into a body tissue and irradiating excitation light corresponding to a fluorescent light wavelength of the reagent upon the body tissue. The light source apparatus 11203 can be configured to supply such narrow-band light and/or excitation light suitable for special light observation as described above.

Figure 22:
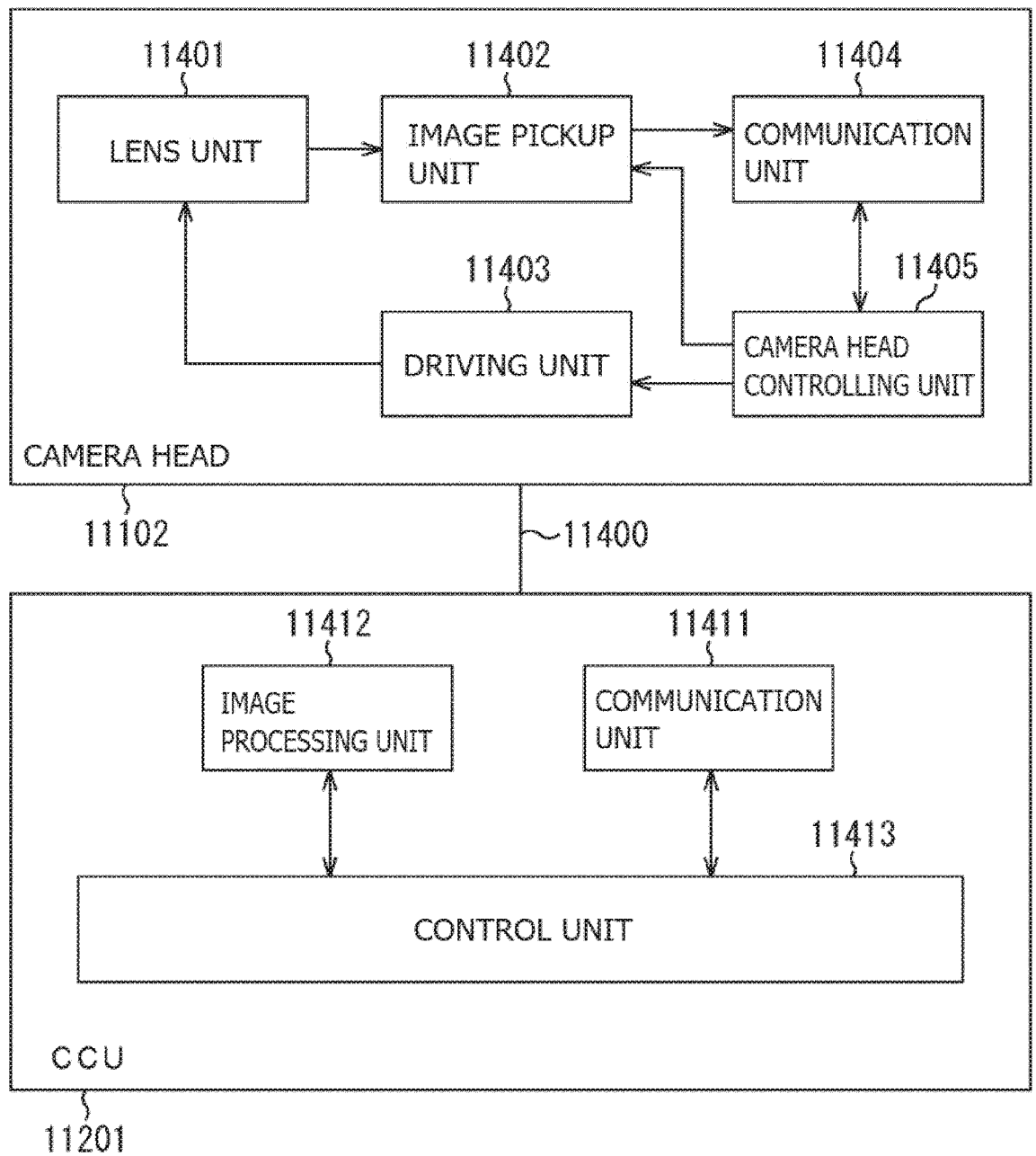
FIG. 22 is a block diagram depicting an example of a functional configuration of a camera head and a camera control unit (CCU).

FIG. 22 is a block diagram depicting an example of a functional configuration of the camera head 11102 and the CCU 11201 depicted in FIG. 21.

The camera head 11102 includes a lens unit 11401, an image pickup unit 11402, a driving unit 11403, a communication unit 11404 and a camera head controlling unit 11405. The CCU 11201 includes a communication unit 11411, an image processing unit 11412 and a control unit 11413. The camera head 11102 and the CCU 11201 are connected for communication to each other by a transmission cable 11400.

The lens unit 11401 is an optical system, provided at a connecting location to the lens barrel 11101. Observation light taken in from a distal end of the lens barrel 11101 is guided to the camera head 11102 and introduced into the lens unit 11401. The lens unit 11401 includes a combination of a plurality of lenses including a zoom lens and a focusing lens.

The number of image pickup elements which is included by the image pickup unit 11402 may be one (single-plate type) or a plural number (multi-plate type). Where the image pickup unit 11402 is configured as that of the multi-plate type, for example, image signals corresponding to respective R, G and B are generated by the image pickup elements, and the image signals may be synthesized to obtain a color image. The image pickup unit 11402 may also be configured so as to have a pair of image pickup elements for acquiring respective image signals for the right eye and the left eye ready for three dimensional (3D) display. If 3D display is performed, then the depth of a living body tissue in a surgical region can be comprehended more accurately by the surgeon 11131. It is to be noted that, where the image pickup unit 11402 is configured as that of stereoscopic type, a plurality of systems of lens units 11401 are provided corresponding to the individual image pickup elements.

Further, the image pickup unit 11402 may not necessarily be provided on the camera head 11102. For example, the image pickup unit 11402 may be provided immediately behind the objective lens in the inside of the lens barrel 11101.

The driving unit 11403 includes an actuator and moves the zoom lens and the focusing lens of the lens unit 11401 by a predetermined distance along an optical axis under the control of the camera head controlling unit 11405. Consequently, the magnification and the focal point of a picked up image by the image pickup unit 11402 can be adjusted suitably.

The communication unit 11404 includes a communication apparatus for transmitting and receiving various kinds of information to and from the CCU 11201. The communication unit 11404 transmits an image signal acquired from the image pickup unit 11402 as RAW data to the CCU 11201 through the transmission cable 11400.

In addition, the communication unit 11404 receives a control signal for controlling driving of the camera head 11102 from the CCU 11201 and supplies the control signal to the camera head controlling unit 11405. The control signal includes information relating to image pickup conditions such as, for example, information that a frame rate of a picked up image is designated, information that an exposure value upon image picking up is designated and/or information that a magnification and a focal point of a picked up image are designated.

It is to be noted that the image pickup conditions such as the frame rate, exposure value, magnification or focal point may be designated by the user or may be set automatically by the control unit 11413 of the CCU 11201 on the basis of an acquired image signal. In the latter case, an auto exposure (AE) function, an auto focus (AF) function and an auto white balance (AWB) function are incorporated in the endoscope 11100.

The camera head controlling unit 11405 controls driving of the camera head 11102 on the basis of a control signal from the CCU 11201 received through the communication unit 11404.

The communication unit 11411 includes a communication apparatus for transmitting and receiving various kinds of information to and from the camera head 11102. The communication unit 11411 receives an image signal transmitted thereto from the camera head 11102 through the transmission cable 11400.

Further, the communication unit 11411 transmits a control signal for controlling driving of the camera head 11102 to the camera head 11102. The image signal and the control signal can be transmitted by electrical communication, optical communication or the like.

The image processing unit 11412 performs various image processes for an image signal in the form of RAW data transmitted thereto from the camera head 11102.

The control unit 11413 performs various kinds of control relating to image picking up of a surgical region or the like by the endoscope 11100 and display of a picked up image obtained by image picking up of the surgical region or the like. For example, the control unit 11413 creates a control signal for controlling driving of the camera head 11102.

Further, the control unit 11413 controls, on the basis of an image signal for which image processes have been performed by the image processing unit 11412, the display apparatus 11202 to display a picked up image in which the surgical region or the like is imaged. Thereupon, the control unit 11413 may recognize various objects in the picked up image using various image recognition technologies. For example, the control unit 11413 can recognize a surgical tool such as forceps, a particular living body region, bleeding, mist when the energy device 11112 is used and so forth by detecting the shape, color and so forth of edges of objects included in a picked up image. The control unit 11413 may cause, when it controls the display apparatus 11202 to display a picked up image, various kinds of surgery supporting information to be displayed in an overlapping manner with an image of the surgical region using a result of the recognition. Where surgery supporting information is displayed in an overlapping manner and presented to the surgeon 11131, the burden on the surgeon 11131 can be reduced and the surgeon 11131 can proceed with the surgery with certainty.

The transmission cable 11400 which connects the camera head 11102 and the CCU 11201 to each other is an electric signal cable ready for communication of an electric signal, an optical fiber ready for optical communication or a composite cable ready for both of electrical and optical communications.

Here, while, in the example depicted, communication is performed by wired communication using the transmission cable 11400, the communication between the camera head 11102 and the CCU 11201 may be performed by wireless communication.

While the endoscopic surgery system has been described here by way of example, the technology according to the present disclosure may be also applied to a microsurgery system and the like, for example.

<Application Example to Mobile Body>

The technology according to the present disclosure is applicable to various products. For example, the technology according to the present disclosure may be implemented as a device mounted on a mobile body of any type such as a car, an electric car, a hybrid electric car, a motorcycle, a bicycle, a personal mobility, an airplane, a drone, a vessel, and a robot.

Figure 23:
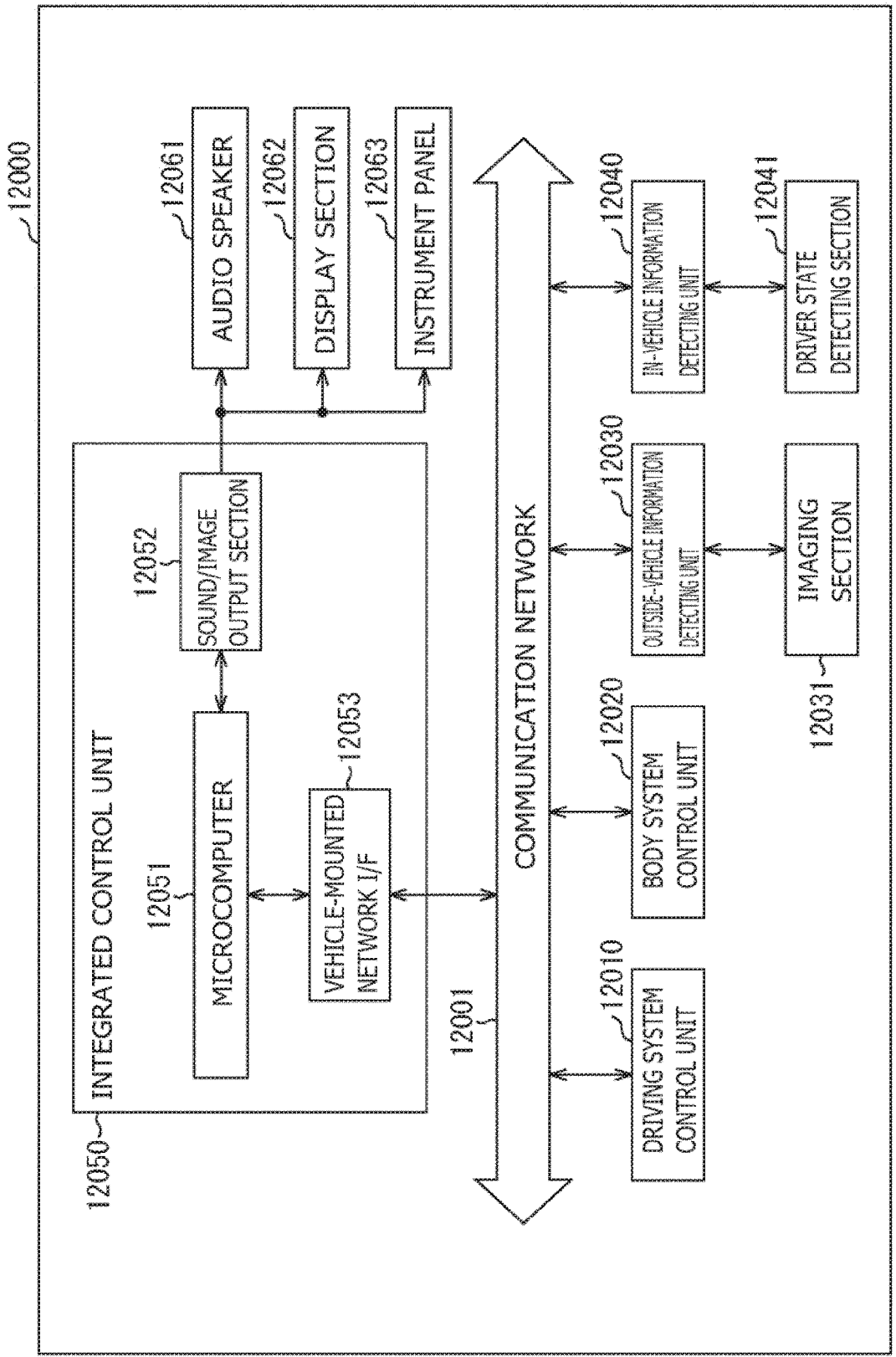
FIG. 23 is a block diagram depicting an example of schematic configuration of a vehicle control system.

FIG. 23 is a block diagram depicting an example of schematic configuration of a vehicle control system as an example of a mobile body control system to which the technology according to an embodiment of the present disclosure can be applied.

The vehicle control system 12000 includes a plurality of electronic control units connected to each other via a communication network 12001. In the example depicted in FIG. 23, the vehicle control system 12000 includes a driving system control unit 12010, a body system control unit 12020, an outside-vehicle information detecting unit 12030, an in-vehicle information detecting unit 12040, and an integrated control unit 12050. In addition, a microcomputer 12051, a sound/image output section 12052, and a vehicle-mounted network interface (I/F) 12053 are illustrated as a functional configuration of the integrated control unit 12050.

The driving system control unit 12010 controls the operation of devices related to the driving system of the vehicle in accordance with various kinds of programs. For example, the driving system control unit 12010 functions as a control device for a driving force generating device for generating the driving force of the vehicle, such as an internal combustion engine, a driving motor, or the like, a driving force transmitting mechanism for transmitting the driving force to wheels, a steering mechanism for adjusting the steering angle of the vehicle, a braking device for generating the braking force of the vehicle, and the like.

The body system control unit 12020 controls the operation of various kinds of devices provided to a vehicle body in accordance with various kinds of programs. For example, the body system control unit 12020 functions as a control device for a keyless entry system, a smart key system, a power window device, or various kinds of lamps such as a headlamp, a backup lamp, a brake lamp, a turn signal, a fog lamp, or the like. In this case, radio waves transmitted from a mobile device as an alternative to a key or signals of various kinds of switches can be input to the body system control unit 12020. The body system control unit 12020 receives these input radio waves or signals, and controls a door lock device, the power window device, the lamps, or the like of the vehicle.

The outside-vehicle information detecting unit 12030 detects information about the outside of the vehicle including the vehicle control system 12000. For example, the outside-vehicle information detecting unit 12030 is connected with an imaging section 12031. The outside-vehicle information detecting unit 12030 makes the imaging section 12031 image an image of the outside of the vehicle, and receives the imaged image. On the basis of the received image, the outside-vehicle information detecting unit 12030 may perform processing of detecting an object such as a human, a vehicle, an obstacle, a sign, a character on a road surface, or the like, or processing of detecting a distance thereto.

The imaging section 12031 is an optical sensor that receives light, and which outputs an electric signal corresponding to a received light amount of the light. The imaging section 12031 can output the electric signal as an image, or can output the electric signal as information about a measured distance. In addition, the light received by the imaging section 12031 may be visible light, or may be invisible light such as infrared rays or the like.

The in-vehicle information detecting unit 12040 detects information about the inside of the vehicle. The in-vehicle information detecting unit 12040 is, for example, connected with a driver state detecting section 12041 that detects the state of a driver. The driver state detecting section 12041, for example, includes a camera that images the driver. On the basis of detection information input from the driver state detecting section 12041, the in-vehicle information detecting unit 12040 may calculate a degree of fatigue of the driver or a degree of concentration of the driver, or may determine whether the driver is dozing.

The microcomputer 12051 can calculate a control target value for the driving force generating device, the steering mechanism, or the braking device on the basis of the information about the inside or outside of the vehicle which information is obtained by the outside-vehicle information detecting unit 12030 or the in-vehicle information detecting unit 12040, and output a control command to the driving system control unit 12010. For example, the microcomputer 12051 can perform cooperative control intended to implement functions of an advanced driver assistance system (ADAS) which functions include collision avoidance or shock mitigation for the vehicle, following driving based on a following distance, vehicle speed maintaining driving, a warning of collision of the vehicle, a warning of deviation of the vehicle from a lane, or the like.

In addition, the microcomputer 12051 can perform cooperative control intended for automatic driving, which makes the vehicle to travel autonomously without depending on the operation of the driver, or the like, by controlling the driving force generating device, the steering mechanism, the braking device, or the like on the basis of the information about the outside or inside of the vehicle which information is obtained by the outside-vehicle information detecting unit 12030 or the in-vehicle information detecting unit 12040.

In addition, the microcomputer 12051 can output a control command to the body system control unit 12020 on the basis of the information about the outside of the vehicle which information is obtained by the outside-vehicle information detecting unit 12030. For example, the microcomputer 12051 can perform cooperative control intended to prevent a glare by controlling the headlamp so as to change from a high beam to a low beam, for example, in accordance with the position of a preceding vehicle or an oncoming vehicle detected by the outside-vehicle information detecting unit 12030.

The sound/image output section 12052 transmits an output signal of at least one of a sound and an image to an output device capable of visually or auditorily notifying information to an occupant of the vehicle or the outside of the vehicle. In the example of FIG. 23, an audio speaker 12061, a display section 12062, and an instrument panel 12063 are illustrated as the output device. The display section 12062 may, for example, include at least one of an on-board display and a head-up display.

Figure 24:
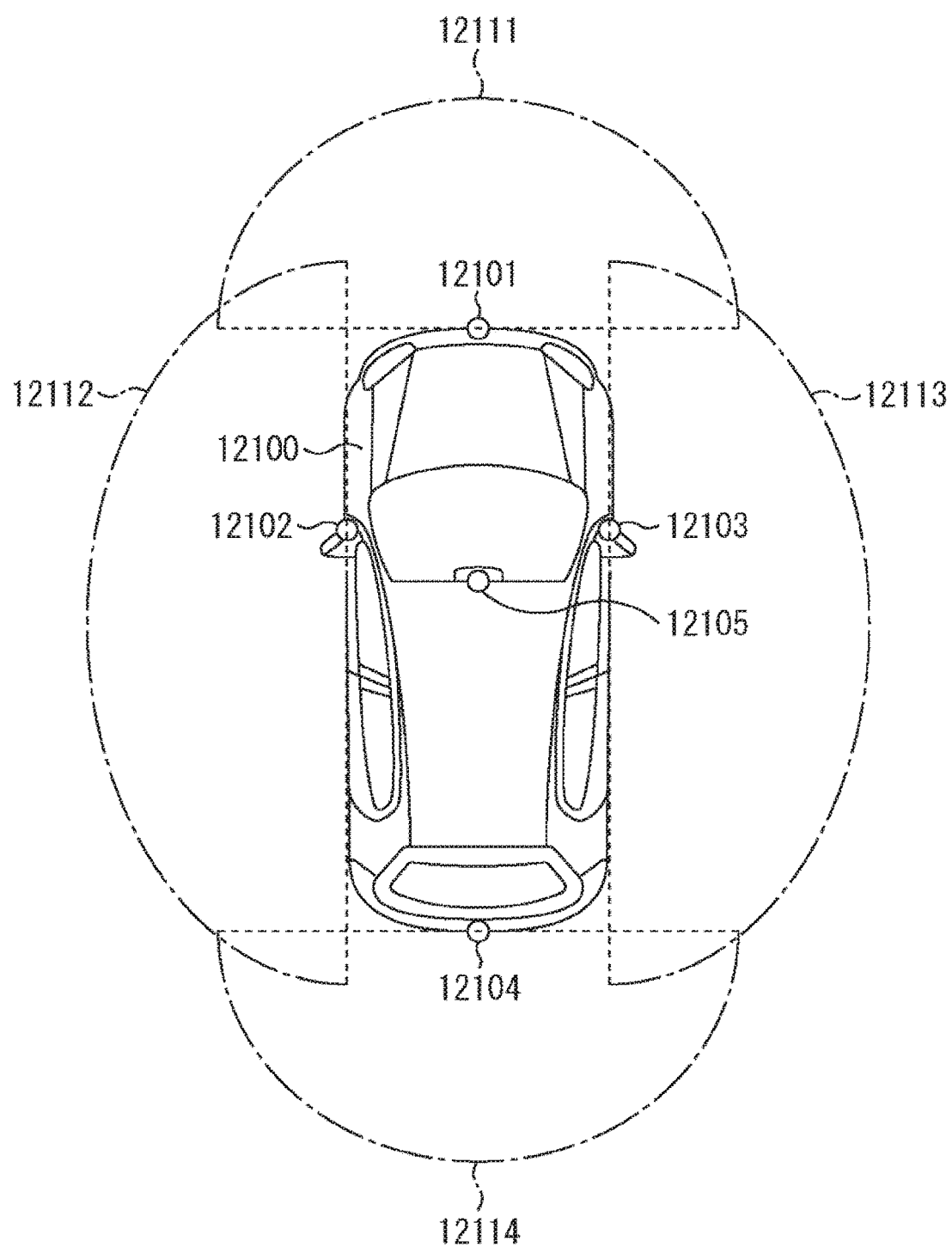
FIG. 24 is a diagram of assistance in explaining an example of installation positions of an outside-vehicle information detecting section and an imaging section.

FIG. 24 is a diagram depicting an example of the installation position of the imaging section 12031.

In FIG. 24, the imaging section 12031 includes imaging sections 12101, 12102, 12103, 12104, and 12105.

The imaging sections 12101, 12102, 12103, 12104, and 12105 are, for example, disposed at positions on a front nose, sideview mirrors, a rear bumper, and a back door of the vehicle 12100 as well as a position on an upper portion of a windshield within the interior of the vehicle. The imaging section 12101 provided to the front nose and the imaging section 12105 provided to the upper portion of the windshield within the interior of the vehicle obtain mainly an image of the front of the vehicle 12100. The imaging sections 12102 and 12103 provided to the sideview mirrors obtain mainly an image of the sides of the vehicle 12100. The imaging section 12104 provided to the rear bumper or the back door obtains mainly an image of the rear of the vehicle 12100. The imaging section 12105 provided to the upper portion of the windshield within the interior of the vehicle is used mainly to detect a preceding vehicle, a pedestrian, an obstacle, a signal, a traffic sign, a lane, or the like.

Incidentally, FIG. 24 depicts an example of photographing ranges of the imaging sections 12101 to 12104. An imaging range 12111 represents the imaging range of the imaging section 12101 provided to the front nose. Imaging ranges 12112 and 12113 respectively represent the imaging ranges of the imaging sections 12102 and 12103 provided to the sideview mirrors. An imaging range 12114 represents the imaging range of the imaging section 12104 provided to the rear bumper or the back door. A bird's-eye image of the vehicle 12100 as viewed from above is obtained by superimposing image data imaged by the imaging sections 12101 to 12104, for example.

At least one of the imaging sections 12101 to 12104 may have a function of obtaining distance information. For example, at least one of the imaging sections 12101 to 12104 may be a stereo camera constituted of a plurality of imaging elements, or may be an imaging element having pixels for phase difference detection.

For example, the microcomputer 12051 can determine a distance to each three-dimensional object within the imaging ranges 12111 to 12114 and a temporal change in the distance (relative speed with respect to the vehicle 12100) on the basis of the distance information obtained from the imaging sections 12101 to 12104, and thereby extract, as a preceding vehicle, a nearest three-dimensional object in particular that is present on a traveling path of the vehicle 12100 and which travels in substantially the same direction as the vehicle 12100 at a predetermined speed (for example, equal to or more than 0 km/hour). Further, the microcomputer 12051 can set a following distance to be maintained in front of a preceding vehicle in advance, and perform automatic brake control (including following stop control), automatic acceleration control (including following start control), or the like. It is thus possible to perform cooperative control intended for automatic driving that makes the vehicle travel autonomously without depending on the operation of the driver or the like.

For example, the microcomputer 12051 can classify three-dimensional object data on three-dimensional objects into three-dimensional object data of a two-wheeled vehicle, a standard-sized vehicle, a large-sized vehicle, a pedestrian, a utility pole, and other three-dimensional objects on the basis of the distance information obtained from the imaging sections 12101 to 12104, extract the classified three-dimensional object data, and use the extracted three-dimensional object data for automatic avoidance of an obstacle. For example, the microcomputer 12051 identifies obstacles around the vehicle 12100 as obstacles that the driver of the vehicle 12100 can recognize visually and obstacles that are difficult for the driver of the vehicle 12100 to recognize visually. Then, the microcomputer 12051 determines a collision risk indicating a risk of collision with each obstacle. In a situation in which the collision risk is equal to or higher than a set value and there is thus a possibility of collision, the microcomputer 12051 outputs a warning to the driver via the audio speaker 12061 or the display section 12062, and performs forced deceleration or avoidance steering via the driving system control unit 12010. The microcomputer 12051 can thereby assist in driving to avoid collision.

At least one of the imaging sections 12101 to 12104 may be an infrared camera that detects infrared rays. The microcomputer 12051 can, for example, recognize a pedestrian by determining whether or not there is a pedestrian in imaged images of the imaging sections 12101 to 12104. Such recognition of a pedestrian is, for example, performed by a procedure of extracting characteristic points in the imaged images of the imaging sections 12101 to 12104 as infrared cameras and a procedure of determining whether or not it is the pedestrian by performing pattern matching processing on a series of characteristic points representing the contour of the object. When the microcomputer 12051 determines that there is a pedestrian in the imaged images of the imaging sections 12101 to 12104, and thus recognizes the pedestrian, the sound/image output section 12052 controls the display section 12062 so that a square contour line for emphasis is displayed so as to be superimposed on the recognized pedestrian. The sound/image output section 12052 may also control the display section 12062 so that an icon or the like representing the pedestrian is displayed at a desired position.

A system in the present description expresses an entire apparatus constituted by a plurality of devices.

Note that advantageous effects to be produced are not limited to the advantageous effects described in the present description presented only by way of example, but may include other advantageous effects.

Note that embodiments of the present technology are not limited to the embodiments described above, but may be modified in various manners without departing from the scope of the subject matters of the present technology.

Note that the present technology can also have following configurations.

(1)

An imaging device including:

a lens that converges object light;

an imaging element that photoelectrically converts the object light received from the lens;

a circuit base that includes a circuit configured to output a signal received from the imaging element to an outside;

an actuator that drives the lens with a PWM (Pulse Width Modulation) waveform in at least either one of an X-axis direction and a Y-axis direction; and plural detection units that are so disposed as to face plural first coils included in the actuator, and detect magnetic fields generated by the first coils.

(2)

The imaging device according to (1) described above, in which the actuator drives the lens to reduce an effect of hand-vibration.

(3)

The imaging device according to (2) described above, in which the actuator also drives the lens in a Z-axis direction that is a direction for shifting a focus.

(4)

The imaging device according to any one of (1) to (3) described above, in which each of the detection units detects induced electromotive force generated by the magnetic fields.

(5)

The imaging device according to (4) described above, in which each of the detection units detects a position of the lens on the basis of the induced electromotive force.

(6)

The imaging device according to any one of (1) to (5) described above, in which each of the detection units detects a position of the lens in a Z-axis direction on the basis of an integrated value obtained by integrating dielectric electromotive force detected by the plural detection units.

(7)

The imaging device according to any one of (1) to (6) described above, in which each of the detection units detects inclination of the lens.

(8)

The imaging device according to any one of (1) to (7) described above, in which each of the detection units detects rotation of the lens.

(9)

The imaging device according to any one of (1) to (8) described above, in which each of the detection units includes a second coil, and center positions of the first coils and center positions of the second coils are not aligned with each other.

(10)

The imaging device according to (9) described above, in which the second coils are asymmetrically disposed with respect to an optical center.

(11)

The imaging device according to (9) or (10) described above, in which magnets are so provided as to face the first coils, and the second coils are located between the first coils and the magnets.

(12)
An electronic apparatus including:
an imaging device including
a lens that converges object light,
an imaging element that photoelectrically converts the object light received from the lens,
a circuit base that includes a circuit configured to output a signal received from the imaging element to an outside,
an actuator that drives the lens with a PWM (Pulse Width Modulation) waveform in at least either one of an X-axis direction and a Y-axis direction, and
plural detection units that are so disposed as to face plural first coils included in the actuator, and detect magnetic fields generated by the first coils.

REFERENCE SIGNS LIST

1 Imaging device, 11 Imaging element, 12 Metal wire, 13 Circuit board, 14 Spacer, 15 Adhesive, 16 Lens, 17 Infrared cut filter, 18 Actuator, 19 Connector, 20 Auto focus driver, 31 FP coil, 32 Position detection coil, 33 Magnet, 41 Board, 50 Detection circuit, 51 Amplification unit, 52 A/D conversion unit, 53 OIS control unit, 54 Control unit

What is claimed is:

1. An imaging device comprising:
a lens that converges object light;
an imaging element that photoelectrically converts the object light received from the lens;
a circuit base that includes a circuit configured to output a signal received from the imaging element to an outside;
an actuator that drives the lens with a PWM (Pulse Width Modulation) waveform in at least either one of an X-axis direction and a Y-axis direction, wherein driving of the PWM waveform is synchronized with a driving signal of the imaging element; and
a plurality of detection units that are so disposed as to face a plurality of first coils included in the actuator, and detect magnetic fields generated by the first coils, wherein each of the plurality of detection units is larger than each of the plurality of first coils.

2. The imaging device according to claim 1, wherein the actuator drives the lens to reduce an effect of hand-vibration.

3. The imaging device according to claim 2, wherein the actuator also drives the lens in a Z-axis direction that is a direction for shifting a focus.

4. The imaging device according to claim 1, wherein each of the plurality of detection units detects induced electromotive force generated by the magnetic fields.

5. The imaging device according to claim 4, wherein each of the plurality of detection units detects a position of the lens on a basis of the induced electromotive force.

6. The imaging device according to claim 1, wherein each of the plurality of detection units detects a position of the lens in a Z-axis direction on a basis of an integrated value obtained by integrating dielectric electromotive force detected by the plurality of detection units.

7. The imaging device according to claim 1, wherein each of the plurality of detection units detects inclination of the lens.

8. The imaging device according to claim 1, wherein each of the plurality of detection units detects rotation of the lens.

9. The imaging device according to claim 1, wherein each of the plurality of detection units includes a second coil, and
center positions of the first coils and center positions of the second coils are not aligned with each other.

10. The imaging device according to claim 9, wherein the second coils are asymmetrically disposed with respect to an optical center.

11. The imaging device according to claim 9, wherein magnets are so provided as to face the first coils, and the second coils are located between the first coils and the magnets.

12. An electronic apparatus comprising:
an imaging device including:
a lens that converges object light;
an imaging element that photoelectrically converts the object light received from the lens;
a circuit base that includes a circuit configured to output a signal received from the imaging element to an outside;
an actuator that drives the lens with a PWM (Pulse Width Modulation) waveform in at least either one of an X-axis direction and a Y-axis direction, wherein driving of the PWM waveform is synchronized with a driving signal of the imaging element; and
a plurality of detection units that are so disposed as to face a plurality of first coils included in the actuator, and detect magnetic fields generated by the first coils, wherein each of the plurality of detection units is larger than each of the plurality of first coils.

* * * * *